US006705990B1

(12) United States Patent
Gallant et al.

(10) Patent No.: US 6,705,990 B1
(45) Date of Patent: Mar. 16, 2004

(54) METHOD AND APPARATUS FOR MONITORING PHYSIOLOGIC PARAMETERS OF A LIVING SUBJECT

(75) Inventors: Stuart L. Gallant, San Diego, CA (US); William H. Markle, Laguna Nigel, CA (US)

(73) Assignee: Tensys Medical, Inc., San Diego, CA (US)

( * ) Notice: Subject to any disclaimer, the term of this patent is extended or adjusted under 35 U.S.C. 154(b) by 0 days.

(21) Appl. No.: 09/625,677

(22) Filed: Jul. 25, 2000

(51) Int. Cl.[7] .............................. A61B 5/00; A61B 5/02
(52) U.S. Cl. .................. 600/300; 600/485; 600/490; 600/500; 128/903; 128/904
(58) Field of Search .................... 600/300, 301, 600/485, 452, 500, 493, 513, 520, 484, 490; 128/903, 904, 920; 709/205; 703/11

(56) References Cited

U.S. PATENT DOCUMENTS

| 3,601,120 A | 8/1971 | Massie et al. |
| 3,617,993 A | 11/1971 | Massie et al. |
| 3,663,932 A | 5/1972 | Mount et al. |

(List continued on next page.)

FOREIGN PATENT DOCUMENTS

| EP | 284 095 B1 | 3/1988 |
| EP | 0 342 249 A1 | 5/1988 |
| EP | 0 466 272 A1 | 7/1991 |
| EP | 0595 666 B1 | 9/1993 |
| EP | 0 603 666 A2 | 12/1993 |
| EP | 0818 176 A | 7/1996 |
| FR | 2 758 709 | 7/1998 |
| WO | WO 84 00290 | 2/1984 |
| WO | WO 92/07508 | 10/1991 |
| WO | WO 95 13014 | 5/1995 |
| WO | WO 98 25511 A | 6/1998 |
| WO | WO 98/51211 | 11/1998 |

OTHER PUBLICATIONS

Drzewiecki, G. (1995) "Noninvasive Assessment of Arterial Blood Pressure and Mechanics," The Biomedical Engineering Handbook CRC Press, Boca Raton, FL, pp. 1196–1211.
Boashash, B., et al. (1987) "An Efficient Real–Time Implementation of the Wigner–Ville Distribution," IEEE Trans ASSP 35:1611–1618.
Drzewiecki, G.M., et al. (1985) Generalization of the Transmural Pressure–Area Relation for the F emoral Artery, 7th Annual IEEE EMBS Conference 507.

(List continued on next page.)

Primary Examiner—Eric F. Winakur
Assistant Examiner—David J. McCrosky
(74) Attorney, Agent, or Firm—Gazdzinski & Associates

(57) ABSTRACT

An improved method and apparatus for monitoring a plurality of physiologic parameters associated with a living subject. In one aspect, the invention comprises a monitoring apparatus capable of non-invasively and continuously monitoring the blood pressure, heart rate (ECG), and weight of the subject. The apparatus further includes a display, input device, and one or more communications links such that data and other information may be communicated between the apparatus and one or more remote locations. In one exemplary embodiment, the apparatus comprises a portable monitoring station disposed in the subject's home, which is kept in communication with a remote medical facility via a wireless interface and PSTN or data network. Two-way communications of monitored data, video, audio, and other types of information is provided to facilitate remote care of the subject, and obviate the need for an in-home caregiver or frequent trips to the medical facility. A communications system for exchanging data between the various locations, and computer program allowing such data exchange, are also disclosed.

15 Claims, 15 Drawing Sheets

U.S. PATENT DOCUMENTS

| | | | |
|---|---|---|---|
| 3,675,640 | A | 7/1972 | Gatts |
| 3,791,378 | A | 2/1974 | Hochbert et al. |
| 3,885,551 | A | 5/1975 | Massie |
| 4,109,647 | A | 8/1978 | Stern et al. |
| 4,122,843 | A | 10/1978 | Zdrojkowski |
| 4,127,114 | A | 11/1978 | Bretscher |
| 4,154,231 | A | 5/1979 | Russell |
| 4,239,047 | A | 12/1980 | Griggs, III et al. |
| 4,249,540 | A | 2/1981 | Koyama et al. |
| 4,349,034 | A | 9/1982 | Ramsey, III |
| 4,476,875 | A | 10/1984 | Nilsson et al. |
| 4,566,462 | A | 1/1986 | Janssen |
| 4,590,948 | A | 5/1986 | Nilsson |
| 4,596,254 | A | 6/1986 | Adrian et al. |
| 4,651,747 | A | 3/1987 | Link |
| 4,719,923 | A | 1/1988 | Hartwell et al. |
| 4,754,761 | A | 7/1988 | Ramsey, III et al. |
| 4,771,792 | A | 9/1988 | Seale |
| 4,838,275 | A | 6/1989 | Lee |
| 4,867,170 | A | 9/1989 | Takahashi |
| 4,869,261 | A | 9/1989 | Penaz |
| 4,901,733 | A | 2/1990 | Kaida et al. |
| 4,924,871 | A | 5/1990 | Honeyager |
| 4,960,128 | A | 10/1990 | Gordon et al. |
| 4,974,607 | A * | 12/1990 | Miwa .......................... 128/903 |
| 5,030,956 | A | 7/1991 | Murphy |
| 5,072,733 | A | 12/1991 | Spector et al. |
| 5,094,244 | A | 3/1992 | Callahan et al. |
| 5,119,822 | A | 6/1992 | Niwa |
| 5,158,091 | A | 10/1992 | Butterfield et al. |
| 5,163,438 | A | 11/1992 | Gordon et al. |
| 5,165,416 | A * | 11/1992 | Shinoda et al. ............. 600/485 |
| 5,170,796 | A | 12/1992 | Kobayashi |
| 5,238,000 | A | 8/1993 | Niwa |
| 5,240,007 | A | 8/1993 | Pytel et al. |
| 5,261,412 | A | 11/1993 | Butterfield et al. |
| 5,273,046 | A | 12/1993 | Butterfield et al. |
| 5,309,916 | A * | 5/1994 | Hatschek .................... 600/485 |
| 5,368,039 | A | 11/1994 | Moses |
| 5,439,001 | A | 8/1995 | Butterfield et al. |
| 5,450,850 | A | 9/1995 | Iinuma |
| 5,450,852 | A | 9/1995 | Archibald et al. |
| 5,467,771 | A | 11/1995 | Narimatsu et al. |
| 5,479,928 | A | 1/1996 | Cathignol et al. |
| 5,494,043 | A | 2/1996 | O'Sullivan et al. |
| 5,590,649 | A | 1/1997 | Caro et al. |
| 5,617,867 | A | 4/1997 | Butterfield et al. |
| 5,634,467 | A | 6/1997 | Nevo |
| 5,642,733 | A | 7/1997 | Archibald et al. |
| 5,649,542 | A | 7/1997 | Archibald et al. |
| 5,785,650 | A * | 7/1998 | Akasaka et al. ............. 600/300 |
| 5,810,724 | A | 9/1998 | Gronvall |
| 5,832,924 | A | 11/1998 | Archibald et al. |
| 5,833,618 | A | 11/1998 | Caro et al. |
| 5,848,970 | A | 12/1998 | Voss et al. |
| 5,876,346 | A | 3/1999 | Corso |
| 5,895,359 | A | 4/1999 | Peel, III |
| 5,908,027 | A | 6/1999 | Butterfield et al. |
| 5,916,180 | A | 6/1999 | Cundari et al. |
| 5,919,141 | A | 7/1999 | Money et al. |
| 5,931,791 | A | 8/1999 | Saltzstein et al. |
| 5,938,597 | A | 8/1999 | Stratbucker |
| 5,964,711 | A | 10/1999 | Voss et al. |
| 5,987,519 | A * | 11/1999 | Peifer et al. ................. 709/205 |
| 6,018,677 | A | 1/2000 | Vidrine et al. |
| 6,080,106 | A * | 6/2000 | Lloyd et al. ................. 128/903 |
| 6,105,055 | A * | 8/2000 | Pizano et al. ............... 709/205 |
| 6,171,237 | B1 * | 1/2001 | Avitall et al. ............... 128/920 |
| 6,176,831 | B1 | 1/2001 | Voss et al. |
| 6,228,034 | B1 | 5/2001 | Voss et al. |
| 6,336,900 | B1 * | 1/2002 | Alleckson et al. .......... 128/904 |
| 6,381,562 | B2 * | 4/2002 | Keane .......................... 703/11 |

OTHER PUBLICATIONS

Hoeks, A.P. G., et al. (1985) Transcutaneous Detection of Relative Changes in Artery Diameter, Ultrasound in Med and Bio 11:51–59.

Carson, E.R., et al. (1983) "The Mathemathical Modeling of Metabolic and Endocrine Systems: Model Formulation, Identification, and Validation," John Wiley & Sons, NY, pp. 185–189.

Anderson, E.A., et al. (1989) "Flow–Mediated and Reflex Changes in Large Peripheral Artery Tone in Humans," Circulation 79:93–100.

Hartley, C.J., et al. (1991) "An Ultrasonic Method for Measuring Tissue Displacement: Technical Details and Validation for Measuring Myocardial Thickening," IEEE Trans Biomed, 38:735–747.

Cariou, Alain, et al. (1998) "Noninvasive Cardiac Output Monitoring by Aortic Blood Flow Determination: Evaluation of the Somete Cynemo–3000 System," Critical Care Medicine, vol. 26, No. 12, pp. 2066–2072.

Advertisement for HemoSonic ™100 by Arrow International—licensed under U.S. Patent 5,479,928 listed above.

Mandeep R. Mehra, M.D., et al., "Emergence of Electronic Home Monitoring in Chronic Heart Failure: Rationale, Feasibility, and Early Results with the HomMed Sentry–Observer System," CHF, 2000, 6:137–139.

Application Ser. No. 09/342,542 entitled "Method and Apparatus for the Noninvasive Determination of Arterial Blood Pressure," filed Jun. 29, 1999 (refers to time–frequency methology).

Application Serial No. 09/534,900 entitled "Method and Apparatus for Assessing Hemodynamics Properties Within the Circulatory System of a Living Subject," filed Mar. 23, 2000.

* cited by examiner

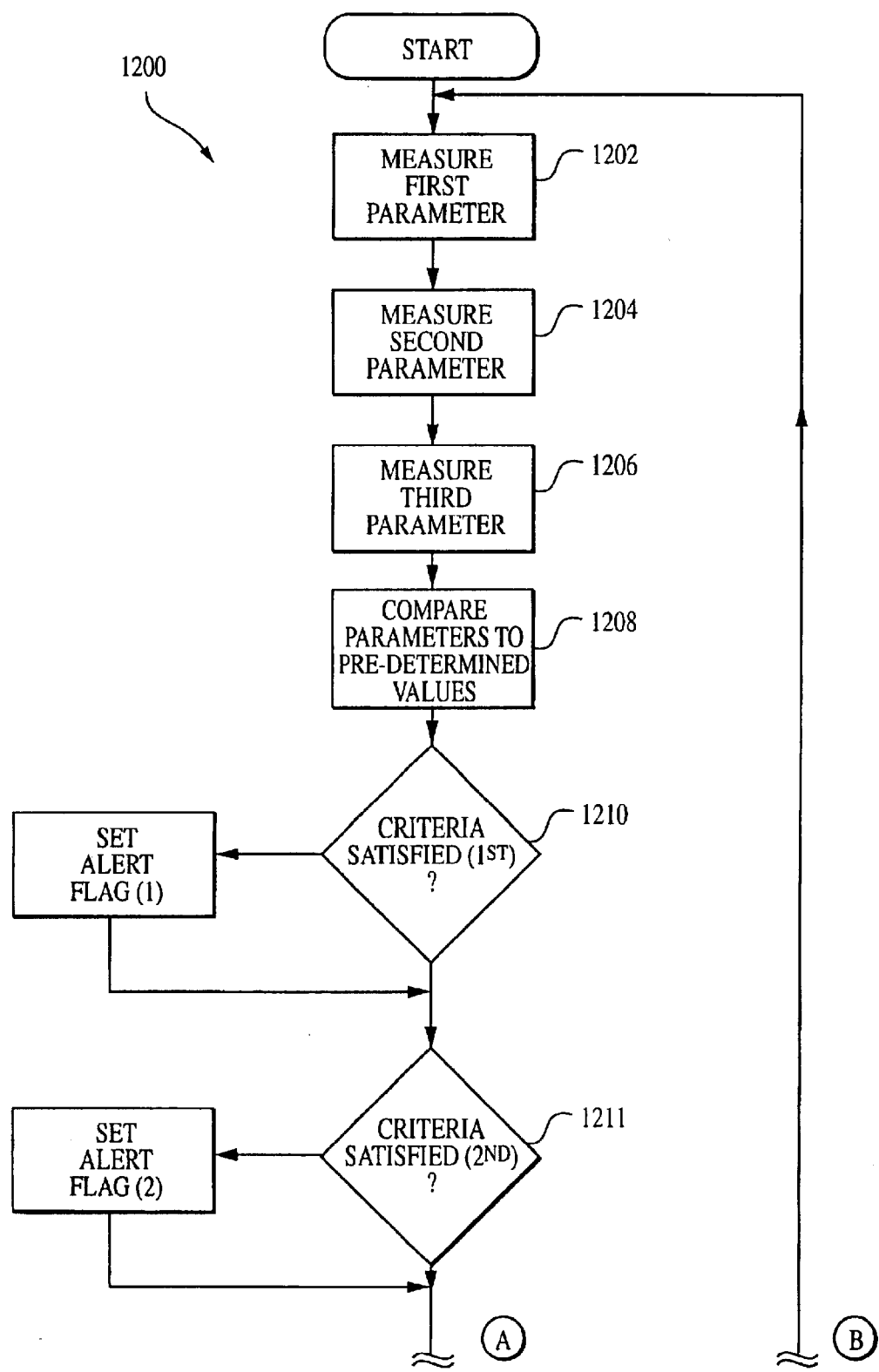

PART 2 OF 2

METHOD AND APPARATUS FOR MONITORING PHYSIOLOGIC PARAMETERS OF A LIVING SUBJECT

RELATED APPLICATIONS

This application is related to U.S. patent applications Ser. No. 09/534,900 entitled "Method And Apparatus For Assessing Hemodynamic Properties Within The Circulatory System Of A Living Subject" filed Mar. 23, 2000, and U.S. patent application Ser. No. 09/342,549 entitled "Method And Apparatus For The Noninvasive Determination Of Arterial Blood Pressure" filed Jun. 29, 1999, both assigned to the Assignee hereof.

This application is a Request for Continued Examination (RCE) of the U.S. patent application No. 09/625,677 of the same title filed Jul. 25, 2000, which is incorporated herein by reference in its entirety.

BACKGROUND OF THE INVENTION

1. Field of the Invention

This invention relates generally to methods and apparatus for monitoring subjects afflicted with various diseases, and specifically to the non-invasive monitoring of physiologic parameters of a subject in the home environment, and communication of this information to a remote location such as a hospital or other medical facility.

2. Description of Related Technology

Congestive heart failure (CHF) is a common, but serious medical condition, which affects hundreds of thousands of people annually. The condition is caused by failure of the heart to function efficiently. In effect, the heart is unable to adequately pump blood throughout the body, which results in a general weakness and lethargy, especially when an individual attempts to exert themselves physically. The greater the severity of the disease, the less capable will be the individual to perform even routine daily activities such as walking, standing, and the like.

Unfortunately, after diagnosis of the condition, which is usually made with a series of tests including cardiac ultrasound, ECG and blood pressure readings, treatment is generally limited to pharmacological therapy including beta-blockers and diuretics to reduce the load on the heart. CHF patients who are otherwise in generally good health are often candidates for heart transplants.

For the majority of patients however, the major challenges are to learn how to alter their lifestyle and live in accordance with the disease limitations. Diet and limited exercise are often prescribed. In addition, a major emphasis is placed on prevention of weight gain, which is often associated with excessive fluid intake or failure to excrete sufficiently, both of which add load to the already failing heart. In many cases, dramatic and rapid changes can occur in an individual, including dyspnea, rapid heart rate and dizziness, if the ejection fraction of the heart falls below certain physiologic limits for a given individual. When this occurs, CHF patients are often emergent cases requiring hospital admission. Subsequently, the typical course of therapy for such patients is increased diuretic therapy to stabilize the situation and them return them to home care.

Medical practitioners generally agree that CHF patients can readily be maintained in their home environment providing that careful monitoring of the key cardiovascular components is routinely performed. Such routine monitoring may be required weekly, daily, or even hourly for certain subjects. Most importantly, the measurement of certain key parameters including weight change, heart rate, and blood pressure would allow for reasonable management of the subject in the home on a day-to-day basis. Changes in peripheral arterial oxygen saturation level, if known, would also be quite useful in the management of the subject. Other parameters relating to the subject's physiology such as basic blood chemistry would also be of use if available. However, under the prior art, no apparatus or techniques exist which provide monitoring of the foregoing physiologic variables of a subject without extensive assistance from a clinician, spouse or other caregiver. Hence, the CHF patient is presently forced to choose between retaining a part- or full-time in-home caregiver, utilizing their spouse extensively (if one exists) as a caregiver, or routinely being transported to a medical facility or visited by a clinician/physician for monitoring. Each of these options has significant drawbacks, ranging from the cost of providing the required care in-home or at the designated medical facility, to the more intangible reduction in quality of life for both the subject and his/her spouse. Clearly, if a CHF (or other) subject could be routinely monitored at home without requiring any significant participation by a caregiver or his/her spouse, then significant benefits in terms of reduced healthcare costs and improved quality of life would be realized.

Another complicating factor in monitoring CHF patients relates to the measurement of blood pressure; routine blood pressure measurements such as those described above can be extraordinarily difficult because of technical limitations associated with current state-of-the-art "cuff" devices, such as those employing the well known auscultation or oscillometry techniques. Specifically, the accuracy of such existing cuff-based blood pressure monitoring devices may be greatly reduced in subjects having low blood pressures and very weak, "thready" (i.e., not steady, or firm) pulses. This reduced accuracy relates in great part to the method by which the cuff devices estimate blood pressure. Furthermore, even if good accuracy is achieved on certain measurements, the clinician or caregiver is left with substantial uncertainty as to which measurements obtained from the subject are accurate or reflective of the actual condition of the subject, and which are not.

Another intrinsic disability of existing blood pressure measurement techniques relates to their non-continuous nature. Specifically, prior art auscultation and oscillometry techniques are geared primarily to "spot" measurement of blood pressure; i.e., at one discrete point in time. As is well known in the medical arts, such spot measurements, even when accurate, may or may not be indicative of the actual physiologic state of the subject. For example, if the blood pressure of the subject is measured during an interval when their blood pressure is artificially increased or depressed, broader trends or patterns in the subject's blood pressure may be masked. As with most any measurement process, observations made on the basis of few data points are generally less reliable and less meaningful than those made on the basis of many data points. In order to obtain a plurality of measurements using the aforementioned prior art techniques, the cuff would need to be inflated and deflated a number of different times, which is very cumbersome and uncomfortable for the subject. Furthermore, repeated inflations of a blood pressure cuff may cause nerve damage to the brachial plexus or damage to the underlying tissues. It is effectively impossible to obtain a truly continuous representation of a subject's blood pressure using these prior art techniques, since there is a practical limit on how rapidly multiple consecutive measurements can be made. Errors due to respiration effects on blood pressure (due largely to the changing volume of the thoracic cavity) may also contribute to the inaccuracy of "spot" blood pressure measurements.

Continuous blood pressure measurements may be made using prior art invasive catheters (commonly known as "A-lines"), however, such devices require the actual surgical implantation of the catheter into the blood vessel of the subject, which is clearly not well suited to long-term daily monitoring of the subject's blood pressure, especially in the home care environment.

In addition to the foregoing, it is often useful to compare values of other physiologic parameters measured concurrently with blood pressure in order to gain a broader perspective on the subject's condition. Prior art blood pressure measurement techniques do not lend themselves well to such simultaneous monitoring, in large part due to the fact that they are "spot" measurements and not continuous in nature. Hence, unless the spot measurement is synchronized to coincide with the other measurements, simultaneous monitoring is not possible. In the context of home healthcare, it is unreasonable to expect a subject (or even a trained caregiver, for that matter) to obtain such synchronized measurements.

Hence, when considered as a whole, the use of cuff-based blood pressure measurement devices on CHF patients (or other subjects with low blood pressure and/or weak, thready pulses) generally produces results which are at best only snapshots of a subject's true blood pressure, and at worst of questionable reliability and poor accuracy. Often, measurements of blood pressure taken by the subject using either automated or semi-automated techniques is questioned by professionals due to its suspected inaccuracy.

Based on the foregoing, what is needed is an improved method and apparatus for assessing a plurality physiologic parameters, including blood pressure, associated with a living subject. Such method and apparatus would ideally (i) be non-invasive, (ii) be integrated such that the monitoring of various parameters could be accomplished simultaneously (or near-simultaneously) and at one physical location so as to minimize discomfort and disturbance to the subject, and (iii) be both useful and produce reliable results under a variety of different subject physiological circumstances, such as for different subjects having a variety of different afflictions. Furthermore, such improved method and apparatus would be capable of monitoring a subject's physiologic parameters in a desired location remote from a hospital or other medical facility (such as in the subject's home), thereby obviating the need for both an in-home caregiver and routine visits by the subject to the hospital/medical facility.

SUMMARY OF THE INVENTION

The present invention satisfies the aforementioned needs by an improved method and apparatus for monitoring physiologic parameters, including blood pressure, within a living subject.

In a first aspect of the invention, an improved apparatus for monitoring a plurality of physiologic parameters of a living subject is disclosed. The apparatus generally comprises a monitoring station having means by which the blood pressure, electrocardiogram (ECG) and heart rate, and weight of the subject may be measured concurrently during a predetermined monitoring interval, and transmitted if desired to a remote location such as a medical facility for analysis or evaluation by a medical professional. In a first embodiment, the monitoring station comprises a support element, at least one ECG probe disposed relative to the support element, a blood pressure monitoring probe adapted for use on the radial artery of the subject, and a scale adapted to measure the weight of the subject while seated on the support element. The ECG probe comprises a pair of conductive handgrips which the subject grasps while seated; a pair of conductive footrests are also optionally provided to measure ECG data from the feet of the subject. The blood pressure monitoring probe is held within an assembly adapted to receive the wrist of the subject, providing access to the radial artery contained therein, when the subject grasps the handgrips. A continuous blood pressure monitoring apparatus is used to provide continuous blood pressure data for the subject during the monitoring interval. The monitoring station is also equipped with (i) a processor for processing data received from the ECG probe(s) and blood pressure probe, (ii) a display for displaying the data obtained during the monitoring interval, (iii) a storage device for storing data for later retrieval and analysis, and (iv) a communications link which allows data obtained from the subject to be transmitted to a remote location, as well as receiving data from the remote location. The monitoring station is also optionally outfitted with a pulse oximeter used to determine the relative percentage arterial oxygen saturation for the subject, and a blood chemistry probe used to perform certain rudimentary blood analyses on a sample of the subject's blood obtained via a pin prick or other comparable technique. In a second embodiment, the monitoring station comprises a platform upon which the subject stands while the aforementioned parameters are monitored. In a third embodiment, the monitoring station is integrated with an exercise device to facilitate monitoring of the subject's physiologic parameters during periods of exercise.

In a second aspect of the invention, an improved system for communicating medical information between a first location and a second, remote location is disclosed. The system generally comprises the aforementioned monitoring station disposed at the first location; a communications terminal (or plurality of terminals) disposed at the second location; and a communications link placing the monitoring station in data communication with the terminal. In a first exemplary embodiment, the communications terminal comprises a personal computer (PC) disposed in a medical facility such as a hospital, and the communications link comprises a pair of modulator/demodulator devices (modems) communicating across a public switched telephone network (PSTN). The modems may comprise digital subscriber line (DSL) modems which operate in conjunction with DSL-capable local loops on respective ends of the communications link to provide enhanced bandwidth. In a second embodiment, the communications terminal comprises a personal computer (PC) disposed in a medical facility such as a hospital, and the communications link comprises video conferencing link (such as that complying with ITU Standard H.323) implemented via a data network. Physiologic monitoring data obtained from the subject at the first location is transmitted to the remote communications terminal via the link and displayed on the terminal's display screen for review by a caregiver; video and/or audio data is also optionally streamed from the monitoring station to the remote terminal (and vice versa) to allow face-to-face communications between the subject and the caregiver. Useful data, such as updated parametric data, analyses of monitored data, calibration data, and the like may also be transmitted from the caregiver to the monitoring station for display and use by the subject in real time. The monitoring station and terminal may also optionally be equipped with text-to-speech (TTS) and/or speech recognition capability to permit the subject and the caregiver to communicate in a variety of forms, such as by the caregiver typing a textual message into their terminal and having the message converted to audio instructions provided to the subject at their monitoring station, or alternatively, the subject providing a verbal report of their present condition, symptoms, etc., and having this report converted to text for inclusion in the data record of the subject reviewed by the caregiver. The operation of the monitoring station may be controlled by the subject using the aforementioned speech recognition system as well.

In a third aspect of the invention, an improved method of remotely monitoring a plurality of physiologic parameters within a living subject is disclosed. The method generally comprises measuring a first physiologic parameter from a blood vessel of the subject; measuring a second physiologic parameter from the subject; measuring a third physiologic parameter from the subject; comparing data derived from the measurements of the first, second, and third physiologic parameters to predetermined values of those parameters, respectively; and identifying when at least a portion of the data bears a predetermined relationship to at least one of the predetermined values. In one exemplary embodiment, the first parameter measured comprises blood pressure, the second heart rate (as derived from ECG measurement), and the third the weight of the subject. Predetermined values or ranges of values acceptable for the given subject are compared to the measurements obtained from the subject via the foregoing apparatus, and the relationship between the measured data and acceptable values/ranges identified.

In a fourth aspect of the invention, an improved method of providing treatment to a subject is disclosed. The method generally comprises the aforementioned method of monitoring the physiologic parameters of the subject, and further includes the steps of transmitting the results of the foregoing comparison to the caregiver at a remote location via a communication channel, analyzing the results at the remote location, and providing a course of treatment for the subject remotely via the communication channel.

In a fifth aspect of the invention, an improved computer program useful for monitoring the physiologic parameters of a subject and embodying the aforementioned methods is disclosed. In one exemplary embodiment, the computer program comprises an object code representation of a source code listing stored on the magnetic storage device of the aforementioned monitoring station, and adapted to run on the microprocessor thereof. In a second embodiment, the program comprises an assembly language/micro-coded instruction set disposed within the embedded storage device, i.e. program memory, of a digital signal processor (DSP) or microprocessor associated with the foregoing monitoring apparatus. In a third embodiment, the computer program comprises an object-oriented distributed application which comprises a plurality of client components distributed at a variety of subject locations, and a server component disposed on a server disposed at a central medical facility, whereby the client components interact and communicate with the server component via one or more data networks.

In a sixth aspect of the invention, an improved display for use in conjunction with the foregoing computer program and apparatus is disclosed. The display generally comprises a display architecture having a plurality of traces relating to respective ones of various physiologic parameters associated with a subject being remotely monitored. The parameters are displayed in temporal format (i.e., value of parameter versus time) for a predetermined monitoring duration, or continuously if desired. Optionally, the display is provided with videoconferencing and/or text messaging windows such that the subject (or conversely, the caregiver) can be viewed, and text messages exchanged, respectively. An analysis window is also provided whereby the results of special analyses performed by the monitoring station, caregiver's communications terminal, or remote analysis equipment may be displayed for viewing by all parties on the network. For example, the monitoring station may be equipped with an algorithm for detecting arrhythmias present in the subject's ECG data; the results of this arrhythmia analysis may be displayed in the aforementioned window. An icon-based touch screen menu structure allows the subject and/or caregiver to rapidly perform a predetermined set of monitoring analysis functions merely by touching the display screen in the appropriate location, including the retrieval of data stored either locally or remotely.

DETAILED DESCRIPTION OF THE INVENTION

Reference is now made to the drawings wherein like numerals refer to like parts throughout.

It is noted that while the invention is described herein in terms of a method and apparatus for monitoring the physiologic parameters of a human subject, including the monitoring of arterial blood pressure via the radial artery, the invention may also be embodied or adapted to monitor such parameters at other locations on the human body, as well as monitoring these parameters on other warm-blooded species. All such adaptations and alternate embodiments are considered to fall within the scope of the claims appended hereto.

It is further noted that the term "caregiver" as used herein is intended to include, inter alia, clinicians, nurses, physicians, specialists, and other medical professionals, as well as those simply providing care and/or assistance to the subject, such as the subject's spouse, relatives, or in-home healthcare worker.

Monitoring Station

Figure 1:
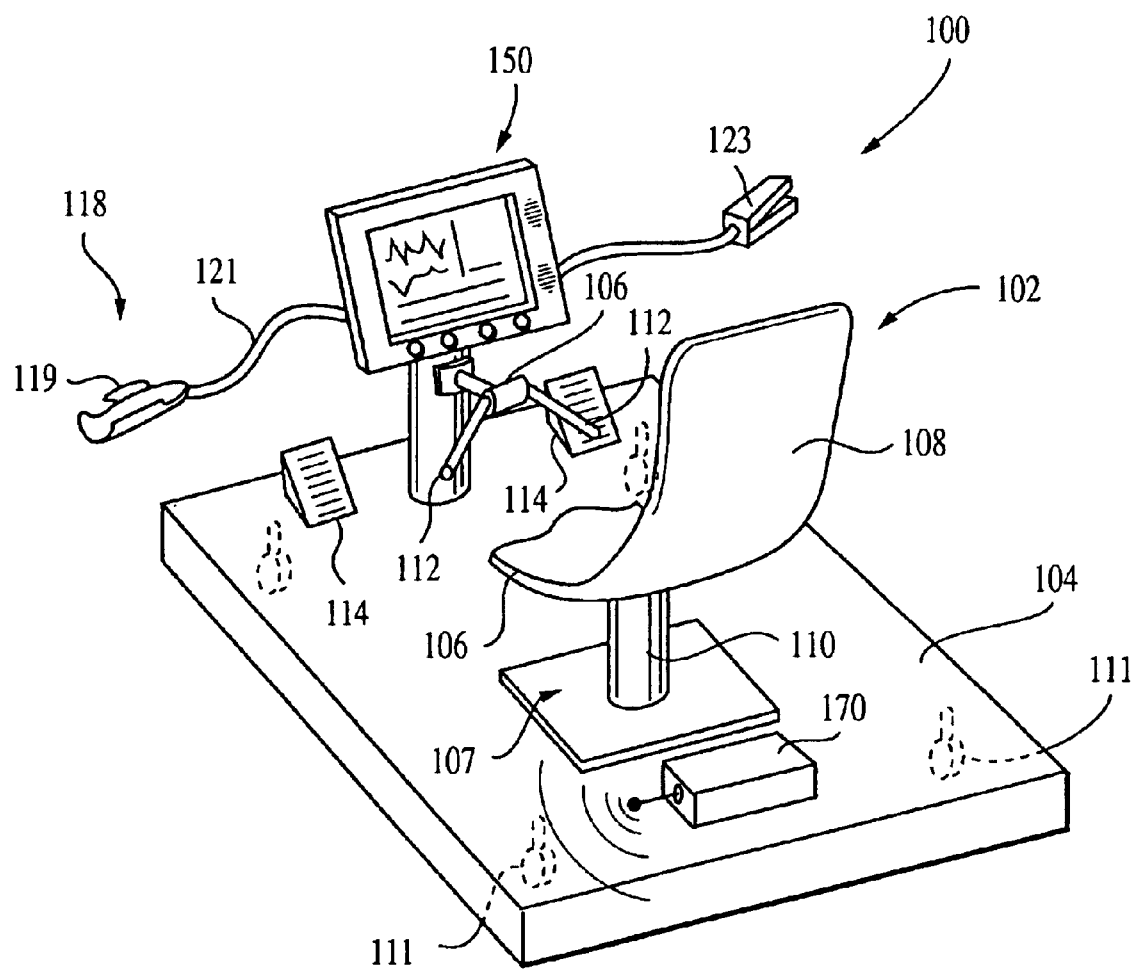
FIG. 1 is a perspective view of a first embodiment of the monitoring station of the present invention, wherein the subject is seated within the station during monitoring.

Referring now to FIG. 1, a first embodiment of the monitoring station of the present invention is now described. As illustrated in FIG. 1 the, monitoring station 100 generally comprises a support element 102, a platform 104, and a handgrip element 106 disposed atop the platform 104. The support element 102 of the present embodiment is a seat-like arrangement having a horizontal section 106 and a substantially vertical or backrest section 108, although it will be recognized that other configurations (such as a simple crossbar or bench) may be used if desired. The support element 102 is coupled to the platform 104 via a vertical stanchion 110, such that the weight of the person sitting in the support element 102 is directly transferred to the platform 104, for reasons discussed further below. The monitoring station of FIG. 1 is generally rigid and also optionally equipped with wheels or casters 111 such that the station 100 may be readily moved from one location to another by the subject or their spouse without significant effort.

The platform 104 of the illustrated embodiment includes an electronic scale 107 or similar weight measurement device that allows the weight of the subject to be obtained simply by the subject sitting in the support element 102. The scale 107 of the illustrated embodiment comprises a digital scale having an accuracy on the order of +/−0.2 lbs, thereby facilitating accurate measurement of the subject's weight, and day-to-day comparison to identify changes or trends therein. The use of a digital scale also permits the scale to be periodically calibrated, such as by a calibration algorithm running on the microprocessor 226 (FIG. 2) which is initiated at startup of the monitoring station, or according to some other predetermined schedule or condition. It will be recognized that many different types of scales having different principles of operation and levels of accuracy may be used consistent with the invention, including analog scales. In the case of an analog scale, the output signal of the scale is converted to the digital domain via an ADC to permit processing by the microprocessor 226, as is known in the electronic arts. The construction and operation of scales is well understood in the prior art, and accordingly is not described further herein.

In addition to the aforementioned scale for measuring subject weight, the platform is further equipped with a handgrip element 106 which is used to obtain electrocardiograph (ECG) information from the subject. The handgrip element 106 includes a pair of conductive substantially horizontal grips 112 which are disposed in front of the support element 102 such that the subject sitting on the support element 102 can readily grasp the conductive grips 112 in a comfortable position while seated. The conductive grips 2 transfer the ECG potential generated by the subject's cardiac system to the processing system 210 (FIG. 2) of the monitoring station 100 for analysis and display, as described in greater detail below. The platform 104 is further optionally outfitted with a pair of conductive footrests 114, which operate in a fashion analogous to the aforementioned handgrips 112, except using the subject's bare feet to measure the ECG potential(s).

It will be recognized that multiple approaches to obtaining ECG data from the subject may be employed consistent with the monitoring station 100 of the present invention. For example, a single, Lead I scalar ECG of the type well known in the medical arts can be obtained by having the subject place their hands around the two conductive grips 112 as previously described. Alternatively, such Lead I ECG can be obtained from the subject while the latter rests their wrists within two contoured and conductive pads built within two arms (not shown) fitted to the support element 102 of the station of FIG. 1. As yet another alternative, multiple scalar ECG leads can be obtained (up to 6) when the subject also places their bare feet on the conductive footrests 114. Under such situations, 6 ECG scalars can be obtained as is conventional with ECG monitoring; Leads I, II and III, and the "augmented" leads including a "VI" lead, a "Vr" lead, and a "Vf" lead. Other alternatives are also possible. In any case, at least one ECG lead can always be obtained from the subject using the present invention.

The monitoring station 100 of FIG. 1 further includes a non-invasive blood pressure monitor 118 for monitoring the blood pressure of the subject. In the illustrated embodiment, the monitor 118 comprises a continuous non-invasive system adapted for use on a blood vessel. (e.g., radial artery) of the subject, such as the hemodynamic. parameter technique described in co-pending U.S. patent application Ser. No. 09/534,900 entitled "Method And Apparatus For Assessing Hemodynamic Properties Within The Circulatory System Of A Living Subject" filed Mar. 23, 2000, and assigned to the assignee hereof, which is incorporated by reference herein in its entirety. This system uses a pressure transducer in conjunction with Doppler ultrasound to measure certain hemodynamic parameters associated with the circulatory system during controlled stenosis, from which a continuous and calibrated measurement of blood pressure is derived. Alternatively, other types of blood pressure monitoring devices may conceivably be used, such as the time-frequency waveform technique described in co-pending U.S. patent application Ser. No. 09/342,549 entitled "Method And Apparatus For The Noninvasive Determination Of Arterial Blood Pressure" filed Jun. 29, 1999, and assigned to the assignee hereof, which is also incorporated by reference herein in its entirety.

By using a continuous, non-invasive system such as those detailed in the above-referenced co-pending applications, the monitoring station 100 of the present invention advantageously can provide calibrated measurements or waveforms of the desired components of the subject's blood pressure over a predetermined interval (as opposed to a discrete point in time), such calibrated measurements also being contemporaneous with other measurements of physiologic parameters made on the subject at the monitoring station (e.g., weight, heart rate, etc.). For example, the apparatus of the present invention may be used to obtain continuous systolic, diastolic, or mean waveforms from the subject Such continuous measurements also free the subject (or caregiver) from having to make multiple measurements using a prior art inflatable cuff device, which can be tedious, uncomfortable, and less than accurate for reasons previously discussed.

Figure 1A:
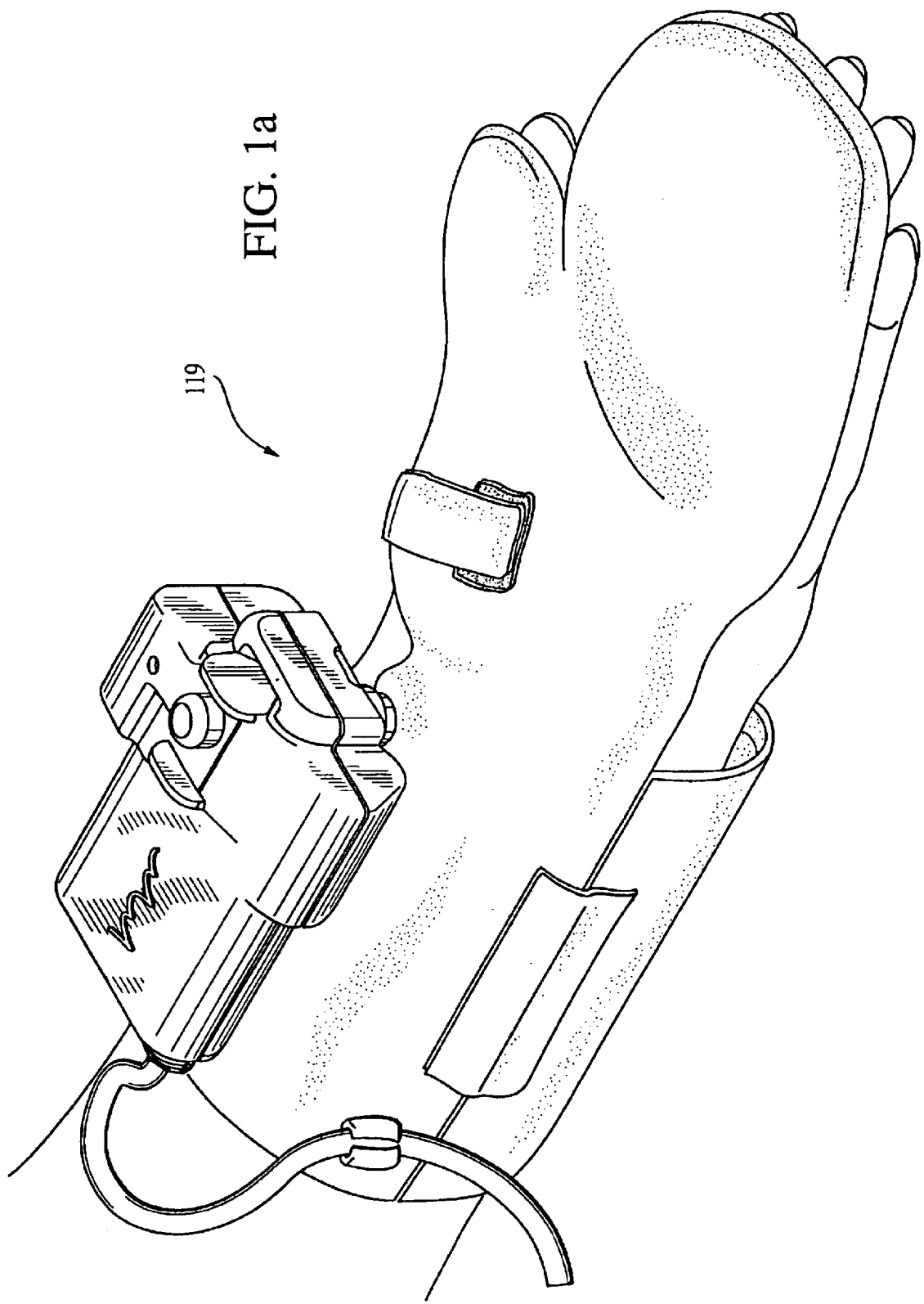
FIG. 1a is a perspective view of one embodiment of the blood pressure monitoring apparatus used in conjunction with the monitoring station of the present invention.

In terms of physical arrangement, the blood pressure monitor 118 of the embodiment of FIG. 1 is adapted to contact the radial artery of the subject during use by way of a wrist brace 119 that is worn by the subject, as shown in FIG. 1a. The brace 119 advantageously allows the subject mobility while being monitored, in that the subject may move their arm and wrist to some degree during the measurement. One embodiment of the brace is disclosed in the aforementioned U.S. patent application Ser. No. 09/342,549 entitled "Method And Apparatus For The Noninvasive Determination Of Arterial Blood Pressure," although it will be recognized that other configurations may be substituted with equal success. For example, the brace 119 could comprise a band or bracelet (not shown) which fits around the wrist area of the subject and is fastened thereto. Alternatively, an artery other than the radial artery of the subject, such as the popliteal or even temporal artery could be used as the basis for the blood pressure measurement. Many other configurations are also possible.

Note that the pressure and ultrasonic sensors present in the blood pressure monitor brace 119 described above may be kept in data communication with the monitoring station 100 using any number of different approaches. For example, one or more insulated cables having metallic (e.g., copper) conductors 121 may be used to exchange data and electrical signals between the monitoring station (i.e., the processing system 210, FIG. 2) and the blood pressure monitor brace 119. Alternatively, a wireless infrared (IR) or radio frequency (RF) transceiver arrangement of the type well known in the art may be substituted, thereby allowing even greater physical freedom. Optical coupling, such as via an optical fiber, may also be used. As yet another alternative, the devices may be coupled inductively or capacitively, such that the electrical and/or magnetic fields generated by one terminal are modulated so as to transfer data across an air gap or other discontinuity, as is also well known in the art.

Alternatively, the blood pressure monitor brace 119 may be configured to be fixed to the monitoring station, such as by having the sensors and a positioning mechanism built into an armrest mounted on the monitoring station 100. In such alternate arrangement, the armrest and brace are configured to receive, orient, and restrain the forearm and wrist of the subject in such a way as to facilitate the measurement of blood pressure from the radial artery; i.e., by guiding or positioning the inner portion of the subjects wrist to be generally in contact with the pressure/acoustic transducers of the blood pressure monitor, where it is then restrained by way of Velcro straps or other similar restraining devices. The aforementioned conductive handgrips 112 may also be positioned immediately adjacent to the brace/armrest in such a way that the subject can comfortably grasp the handgrip 112 when their arm is properly positioned within the brace.

The station 100 of FIG. 1 also optionally includes a pulse oximeter device 123 for measuring the relative percentage arterial oxygen saturation of the subject. As is well known in the art, pulse oximeters measure the relative absorption of certain wavelengths (e.g., infrared) of light by blood cells in the subject's blood stream. The oxygen saturation (SpO2) of the hemoglobin in arterial blood is determined by the relative proportions of oxygenated hemoglobin and oxygen-reduced hemoglobin in the subject's arterial blood. A pulse oximeter calculates the SpO2 value by measuring the difference in the absorption spectra of the oxygenated and reduced hemoglobin. The pulse oximeter includes a probe that is placed in contact with the skin, either on a flat surface (reflectance probes) or across some appendage such as a finger or earlobe (transmission probes). The theory and construction of pulse oximetry devices are well known in the medical device arts, and accordingly are not described further herein.

Figure 1B:
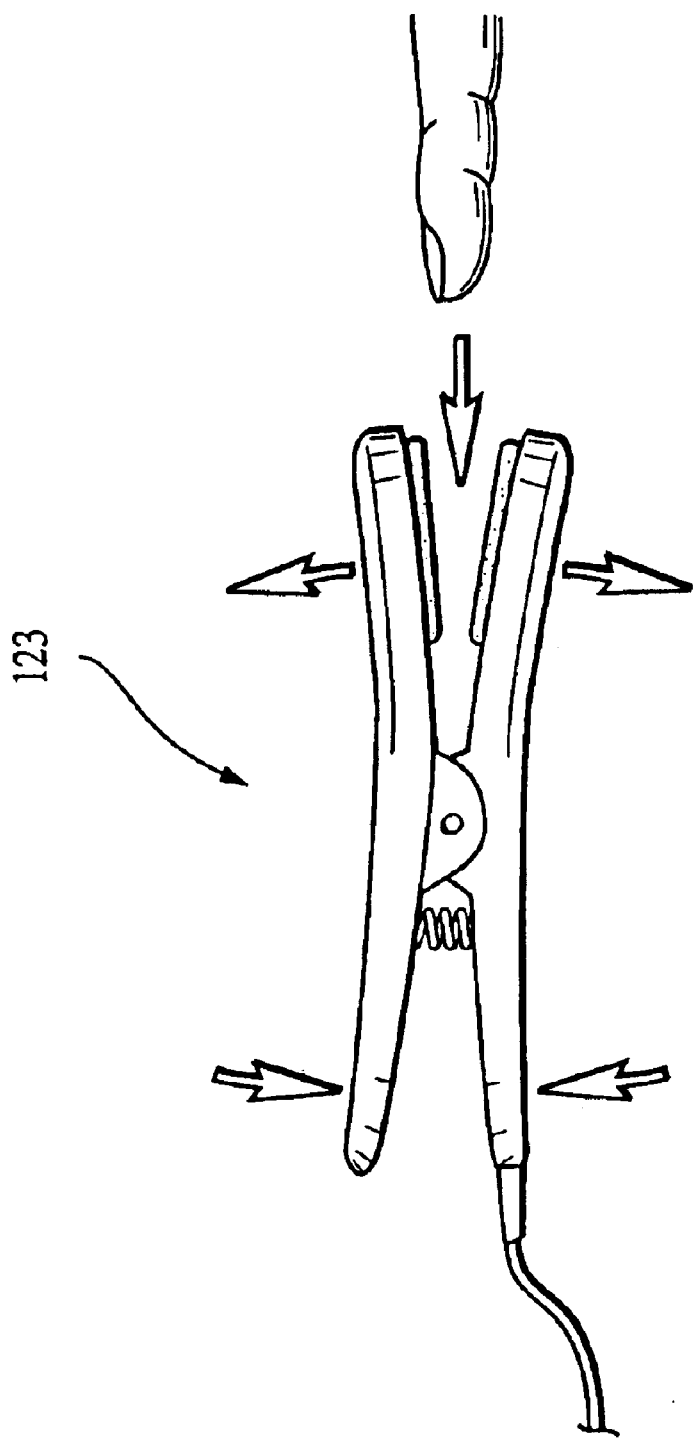
FIG. 1b is a side plan view of one embodiment of the pulse oximeter apparatus used in conjunction with the monitoring station of the present invention.

In the present embodiment, the pulse oximeter comprises a transmission-type finger clamp (FIG. 1b) which fits on the index finger of the subject during monitoring, such as that described in U.S. Pat. No. 5,810,724 entitled "Reusable Sensor Accessory Containing a Conformable Spring Activated Rubber Sleeved Clip," issued Sep. 22, 1998, assigned to Nellcor Puritan Bennett Inc., and incorporated herein by reference in its entirety. It will be recognized, however, that other approaches and configurations may be substituted. For example, one alternative embodiment to the aforementioned finger clamp comprises a hand rest which includes a shaped enclosure into which the index finger of the subject is inserted when the subject's hand is lying upon the hand rest. The enclosure is equipped with the pulse oximetry components (e.g., light source and sensor) and shaped such that when the subject's index finger is positioned fully within the enclosure, the finger is automatically oriented in the proper location with respect to the source and sensor such that oximeter measurements may be obtained. This approach obviates having the subject or other individual clamp the oximeter probe onto and off of the subject's finger; rather, using the aforementioned alternate embodiment, the subject merely pushes their finger in the enclosure, and removes it therefrom when the measurement is completed. As yet another alternative, the source and sensor of the oximeter device may be moved automatically by the monitoring station 100 into the proper position (such as by using a small positioning motor) around the finger when the latter is inserted into the enclosure. Many other such variations are possible, such as taking the oximetry measurements from other locations of the body (e.g., earlobe, toes and the forehead).

In addition to the scale, ECG, blood pressure monitor, and pulse oximeter previously described, the monitoring station 100 may also be optionally outfitted with a blood chemistry probe (not shown). This probe allows the subject to perform basic blood chemistry analyses (including, for example, hematocrit, clotting time, potassium, and sodium levels) during monitoring using a small sample of blood from the subject's finger. In one embodiment, the probe comprises a small pin or other sharp protrusion upon which the subject may prick their finger to extract a drop of blood. The blood is then smeared by the subject onto a slide which is then analyzed via an analyzer. Electrophoresis, photometric methods or ion selective electrochemistry are examples of various techniques used to measure whole blood samples for chemical content. The probe is mounted on the monitoring station 100 at a convenient location whereby the subject may access and operate it readily.

The monitoring station is also equipped with a display device 150 that in the present embodiment comprises a liquid crystal display (LCD) based on a thin film transistor (TFT) matrix, as is well known in the electronic arts. The display device 150 is mounted generally in front of the subject's body and positioned for comfortable viewing, and is used to display, inter alia, data representative of the physiologic parameters monitored, as well as other information pertinent to the subject. As described in greater detail below, the display 150 may be used to provide still frame or video images to the subject and/or caregiver during monitoring, textual messages between the subject and a remote location (such as a remote health care facility), and/or other types of information content such as the results of prior physiologic monitoring periods, news, stock market quotations, entertainment, relaxing images, etc. The display device 150 is also advantageously configured with a capacitive touch screen display of the type well known in the art. By placing their finger at a predetermined location on the screen, the subject may rapidly and easily initiate a variety of monitoring or other functions, as described in greater detail herein with respect to FIG. 8.

It will be recognized that while an LCD/TFT device is used in the illustrated embodiment, other types of display devices, including without limitation a plasma display, cathode ray tube (CRT), or light emitting diode (LED) array, may be used to provide some or all of the display functionality if desired. Alternatively, the display may comprise a head-mounted optical device which displays information to the subject by projecting light through a prism, LCD matrix, or comparable optical medium for close-range viewing by one or both of the subject's eyes. As yet another alternative, the monitoring station 100 may be equipped with a data interface (such as a common 9-pin connector interface) to permit the subject to utilize the monitor associated with their personal computer (PC) to display images and data. Similarly, a data interface adapted to utilize the subject's television set (such as a low- or high-definition TV, or projection TV) or portable electronic device (e.g., PDA, handheld computer) may be provided if desired.

Figure 9:
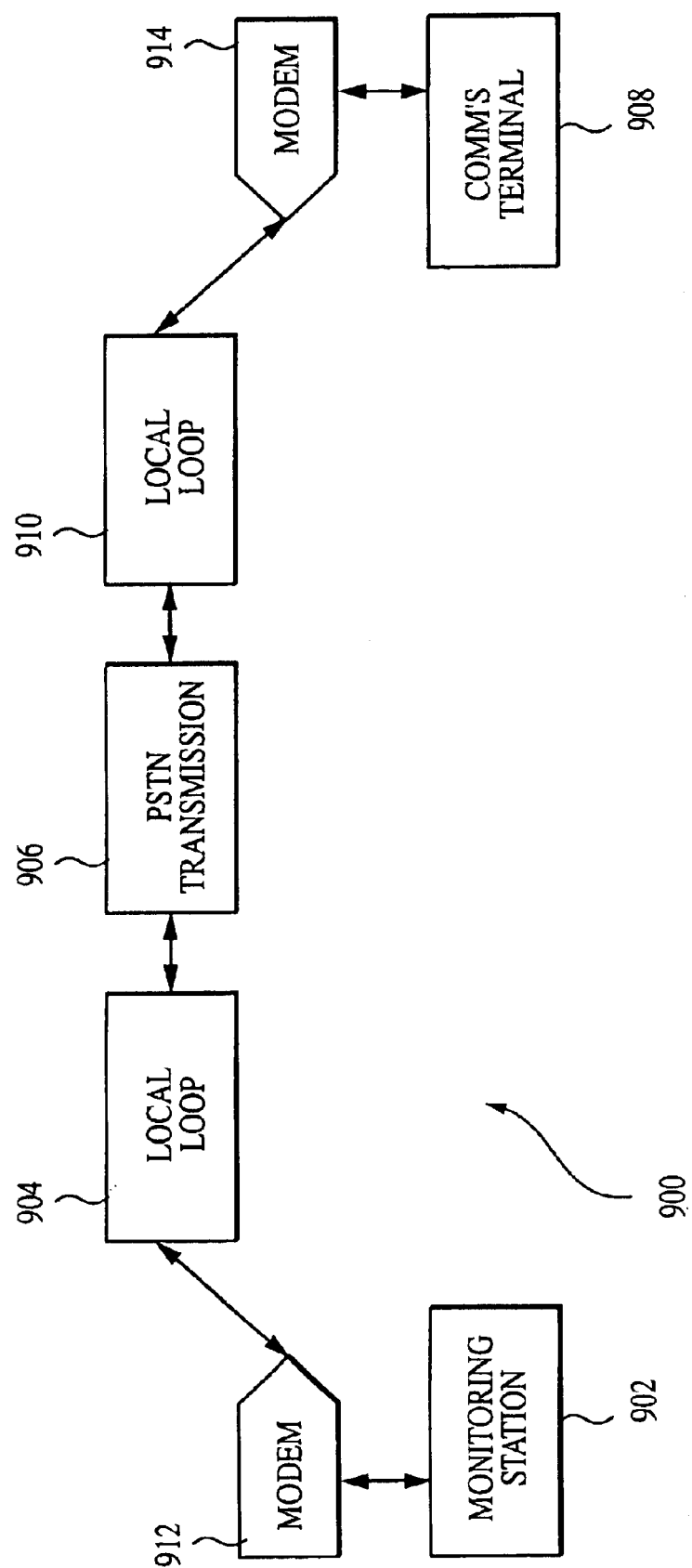
FIG. 9 is a functional block diagram of a first exemplary embodiment of the system for communicating medical information according to the invention, the system employing a public switched telephone network.

The monitoring station 100 of FIG. 1 is further equipped with a communications device 170 which allows for the communication of content between the monitoring station and a remote communications terminal 908 (FIG. 9). As used herein, the term "content" refers to informational or data content contained within a unit or collection of units of information being transmitted. Such content may comprise, without limitation, one or more data packets; a data file; a textual message (SMTP or comparable); a preformatted network administration or communications message (e.g., RTP); an H.320/H.323 audio/video packet stream; a JPEG, tagged image file format (.TIF), graphics interchange format (.GIF), or bitmap (.BMP) image; portable network graphics file (.PNG); computer program; an MP3, .WAV, or LPC/CELP audio file; or an MPEG or .AVI video file. Such content may be rendered in a form cognizable to a human, such as in the case of text file or JPEG image displayed on the display device of a computer, or alternatively be rendered in a machine-readable form (such as a data file or computer program reduced to binary code). The communications device 170 may be a "hardwired" to the communications interface 172 servicing the monitoring station (such as a local loop telephone jack or network interface) within the subject's residence, such as by using a plurality of metallic conductors or optical fibers. Cable and optical based data transfer methods are well understood in the industry.

However, the embodiment of FIG. 1 advantageously uses a wireless radio frequency transceiver arrangement to permit both freedom of movement and data to flow both from the monitoring station 100 to the remote location (via the communications interface 172, as shown in FIG. 9 herein), or vice-versa. A number of different wireless transmission methodologies (air interfaces) may be employed to transfer data between these entities including, inter alia, point to point transmission via the Infrared Data Association's ("IrDA") infrared based wireless transmission standard; wireless radio frequency ("RF") based local area network ("LAN") connections based on the IEEE 802.11 LAN access standard (including both frequency-hopping and direct sequence spread spectrum variants); the "Bluetooth" 2.45 GHz frequency band based wireless communication specification, and the Home RF Shared Wireless Access Protocol. The construction and operation of each of these air interfaces is well known in the communications arts, and accordingly is not described further herein.

Figure 2:
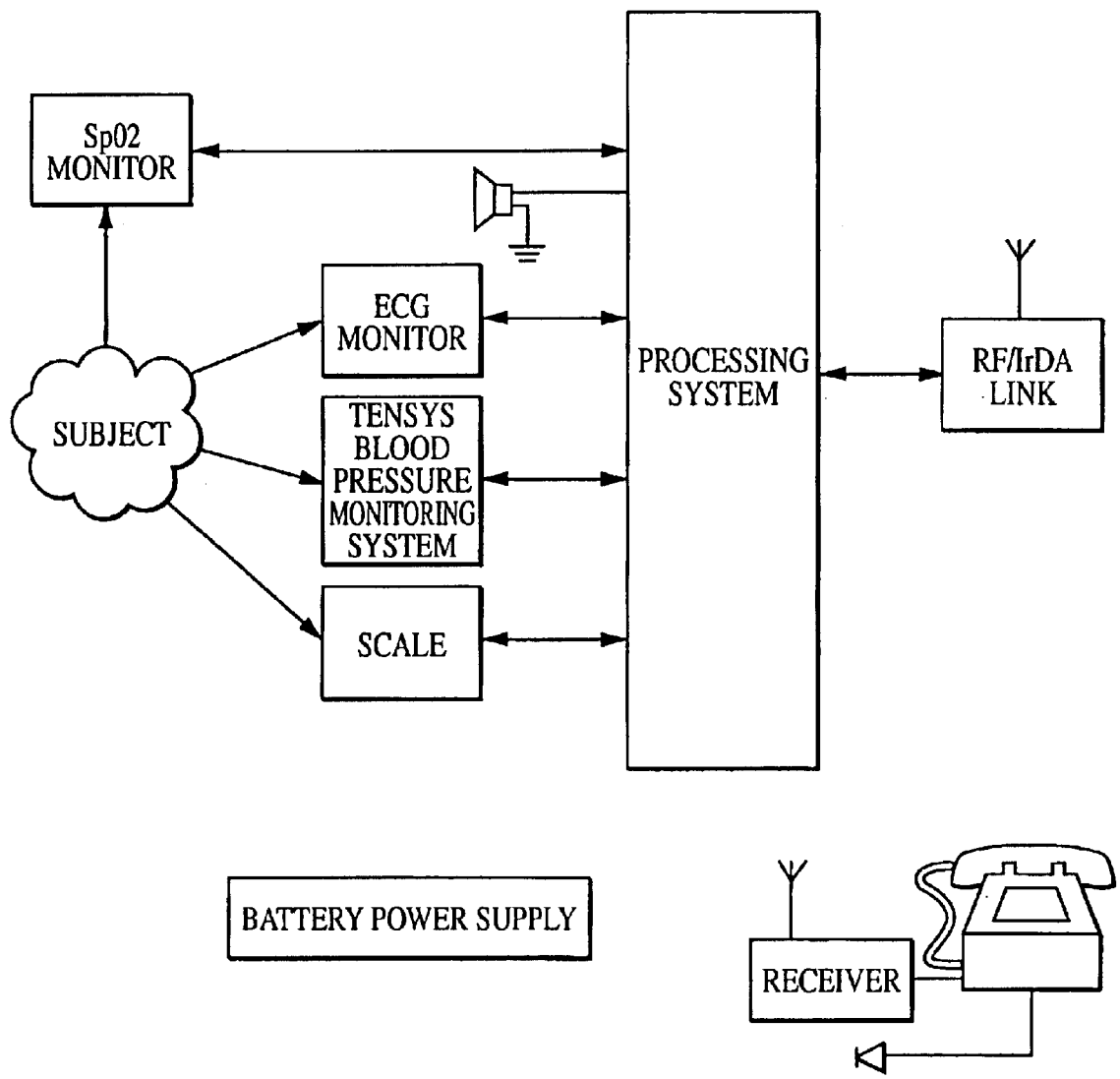
FIG. 2 is a functional block diagram of the apparatus of FIG. 1, illustrating the functional relationships of the various components.

Referring now to FIG. 2, the functional relationship of the various electrical components of the monitoring station of FIG. 1 is described. As shown in FIG. 2, the monitoring station 100 comprises an ECG monitor 202 (including handgrips 106 and/or footrests 114), a blood pressure monitoring system 118, a scale 206, an SpO2 monitor 121, processing system 210, power supply 212, and communications device 170. The station 100 also comprises an audio speaker 218 and display 150. The ECG monitor 202, blood pressure monitor 118, scale 206, and SpO2 monitor 121 are operatively coupled to the processing system 210, the latter processing data and signals obtained from the various aforementioned components for purposes of signal processing and analysis, display on the display unit 150, and ultimately transmission over the communications link 170 if desired. The processing system 210 of the present embodiment comprises a microprocessor 226, micro-controller 227, display driver 228, random access memory 230, program memory 232, DMA 233, analog-to-digital converter (ADC) 234, I/O interfaces 236, and mass storage device 239. An input device 241 is also provided to permit the subject to select various monitoring functions, parameters, settings, etc. In the illustrated embodiment, a plurality of dedicated function keys (not shown) are provided on the input device 241 such that the subject merely selects the desired function (or functionsj by depressing the associated function key(s). Such approach is used to minimize the complexity and likewise maximize the ease of use of the monitoring station for the subject 100, who may be in a state of heightened anxiety during the monitoring session. Such anxiety might be only exacerbated through the need to perform a complex sequence of inputs or keystrokes, thereby potentially affecting the values of the physiologic parameters obtained from the subject during the monitoring period.

The microprocessor 226 and micro-controller 227 are programmed such that data may be obtained from the blood pressure monitor 118, scale 206, SpO2 monitor 121, and ECG probes 112, 114 both continuously and simultaneously. Data is displayed on the display unit 150 via the display driver 228, and stored if desired in the memory 230 or mass storage device 239 if desired. A predetermined monitoring interval is specified by the programmer (or alternatively by the subject via an attached input device 241, or even the caregiver from a remote location via the communications device 170) in which data is obtained from each or a subset of the aforementioned monitors and displayed/stored. In one embodiment, the interval is set at 60 seconds, and the processing system 210 obtains data from the scale, SpO2, blood pressure monitor, and ECG probes during the entirety of the interval. The collection of data may be delayed and/or synchronized on a monitor-by-monitor basis to permit contemporaneous storage and display, or alternatively data may be stored temporarily in the RAM 230 and subsequently retrieved for display/analysis. For example, the processing system 210 may store data obtained from various monitors in RAM until all data has been collected; at this point, all of the data is retrieved and contemporaneously displayed on the display unit 150 and transmitted via the communications device 170 to a remote site.

The processing system 210 is also optionally equipped with an analysis module (not shown) in the form of a computer program running on the microprocessor 226 of the processing system. The analysis module is configured to perform (i) arrhythmia analysis, (ii) ST segment analysis and (iii) analysis of the subject's pacemaker functionality; and (iv) error detection (such as when the subject's finger is not properly received within the pulse oximetry probe, thereby producing an erroneous reading). Specifically, electrical signals generated by the subject as part of the ECG measurement and analysis previously described are digitized using the ADC 234 and analyzed using algorithms running on the aforementioned processor(s) which are adapted to identify patterns or anomalies with the subjects cardiac rhythm or pacemaker For example, the presence of ventricular arrhythmias, such as ventricular tachycardia, or even frequent ectopy, in CHF patients may lead to potential serious sequalae, in that serious arrhythmias further compromise cardiac output. In many subjects, atrial fibrillation may also be present which has serious consequences related to stroke, further exacerbating the CHF patient's long term prognosis. Such algorithms are useful for, inter alia, identifying problem conditions within the subject which may otherwise go unrecognized by the subject or the caregiver. For example, the subject's heart rate as measured from the ECG data may be within the prescribed allowable band, but may contain significant arrhythmias or irregularities which be hazardous to the subject if appropriate action is not taken. Similarly, a malfunction in the subject's pacemaker (if present) may be detectable by analyzing the ECG data. The structure and operation of algorithms useful in identifying these types of exemplary conditions are well known in the medical software arts, and accordingly are not described further herein.

The monitoring station 100 further includes a power supply 247 which supplies electrical power to the various components. A rechargeable alkaline battery of the type well known in the art is used in the invention to facilitate ease of operation as well as the portability of the station 100. It is noted, however, that while the power source for the station 100 of FIG. 1 comprises a rechargeable alkaline battery, such power source may take any one of a number of different forms. For example, non-rechargeable batteries may be substituted. Alternatively, an alternating current (AC) power supply, such as the 60 Hz/115 Vac sources common in households, may be used. As yet another alternative, a wireless inductive charging system (such as those commonly found on electric vehicles or rechargeable appliances) may be used, wherein the subject simply inserts an inductive probe into a specially shaped receptacle for a period of time. The station 100 may be partially or completely solar powered. Myriad other alternative power sources can conceivably be used as well. All such power sources are well known in the electrical arts, and therefore are not described further herein.

Figure 3:
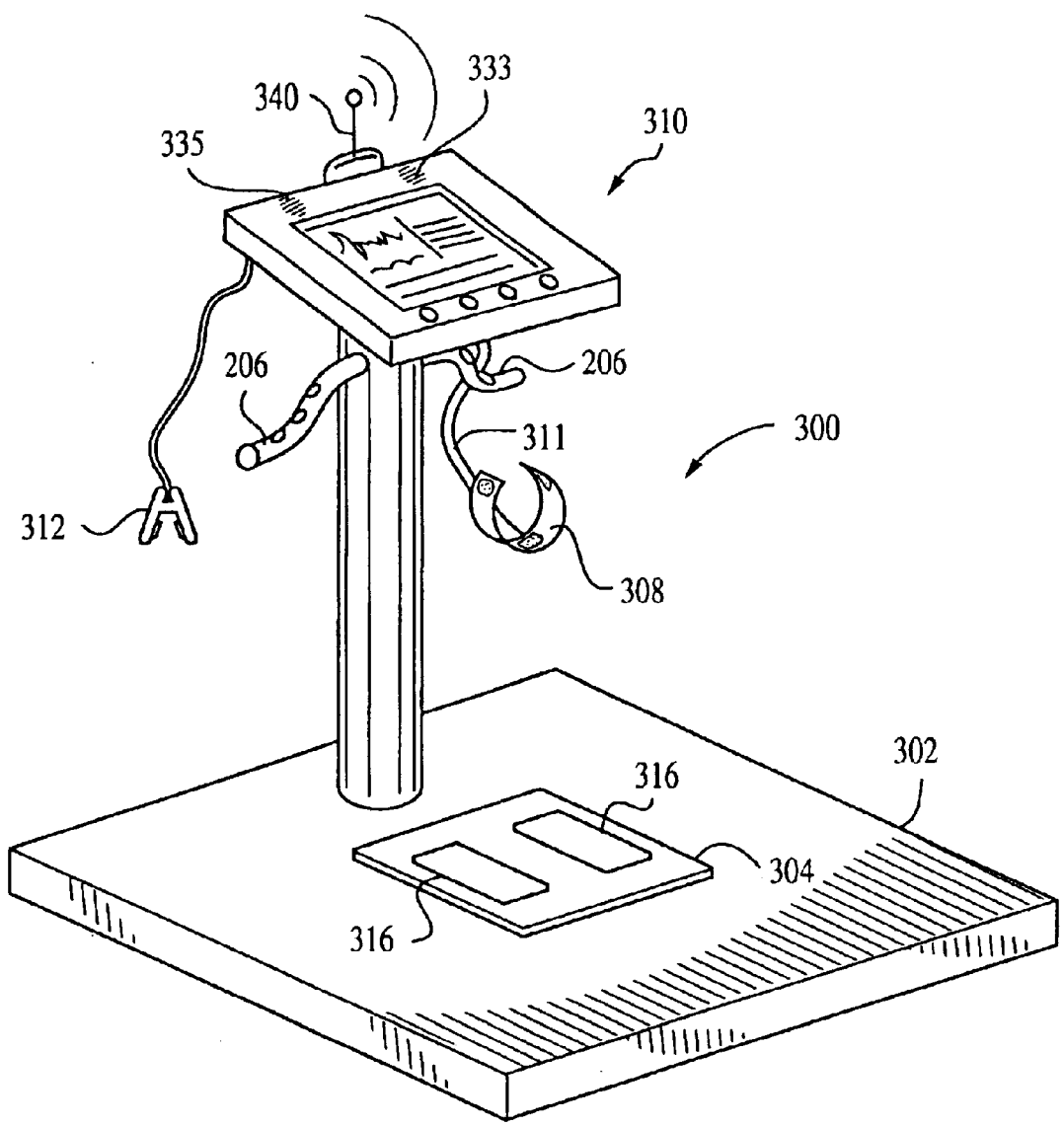
FIG. 3 is a perspective view of a second embodiment of the monitoring station of the present invention, wherein the subject stands within the station during monitoring.

Referring now to FIG. 3, a second embodiment of the monitoring station is described. As illustrated in FIG. 3, the station 300 comprises generally a base platform 302, a scale platform 304 upon which the subject stands, a handgrip element 206, a blood pressure monitor 308 interfacing with the monitoring station via a cable 311, a display unit 310, and an optional pulse oximeter 312 and blood chemistry probe (not shown). The display 310 is oriented such that it is viewable by the subject while standing on the scale platform 304, and includes an integral speaker 333 and microphone 335, as well as a wireless communications link 340 for transmitting data to and from the station 300. The scale platform 304 is also outfitted with a set of conductive foot pads 316 upon which the subject stands when being monitored; these act as additional ECG probes as analogous to the operation of the conductive footrests 114 of FIG. 1. Other than the aforementioned changes in the physical configuration and position of the various components, the operation of the monitoring station of FIG. 3 is completely analogous to that of FIG. 1 as described above.

Figure 4:
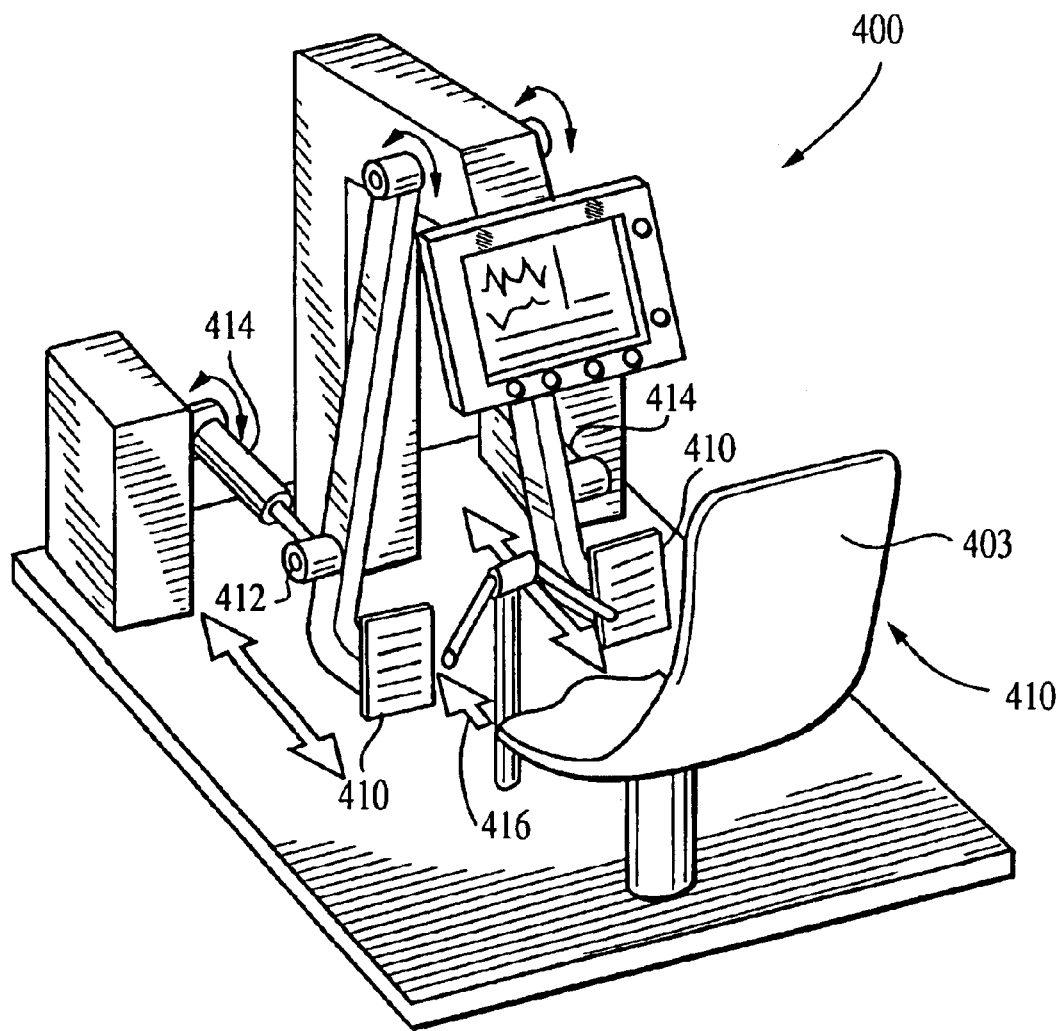
FIG. 4 is a perspective view of a third embodiment of the monitoring station of the present invention, wherein the station is integrated with exercise equipment in order to facilitate the measurement of physiologic parameters during exercise.

FIG. 4 illustrates a third embodiment of the monitoring station of the present invention. As shown in FIG. 4, this third embodiment of the station 400 comprises each of the aforementioned monitoring devices including blood pressure monitor, scale, ECG, pulse oximeter, and blood chemistry probe, yet further includes exercise equipment capable of stimulating the subject's cardiovascular system during monitoring. Specifically, the station 400 includes two movable conductive footrests 410 in place of the stationary conductive footrests 114 of the embodiment of FIG. 1. These movable footrests 410 are coupled via a hinge and pin arrangement 412 or other rotatable assembly (such as a ball joint or Heim joint) to a resistance mechanism 414; the resistance mechanism 414 provides the resistance to the normal force 416 applied by the subject's feet to the footrests 410 during exercise. The backrest 403 of the support element 410, as well as friction against the support element 401 due to the weight of the subject, both provide counter to the reaction force generated by the subject during exercise. As is well known in the art, these resistance mechanisms may be constant or progressive in nature, and may comprise any number of different configurations such as damped and pressurized fluidic or gaseous cylinders, springs, gear and cam arrangements, compressible solids, elastomer bands, etc. Damped pressurized oil cylinders of the type well known in the art are chosen in the present embodiment, due to their progressive resistance as a function of compression rate, and reverse damping characteristics (i.e., ability for the subject to remove their foot from the footrest 410 without experiencing a rapid movement or backlash of the footrest).

The resistance mechanisms 414 may also be electronically controlled, such as by the processing system 210 previously described, so as to allow the subject (or alternatively the caregiver present at a remote location) to vary the resistance of the mechanisms 414 according to a predetermined profile or pattern. For example, after observing the values of the subject's blood pressure, ECG, and SpO2 during a resting or relaxed state, a physician located at a location remote from the subject may desire to monitor these physiologic parameters under certain other levels of cardiovascular output. Accordingly, the physician may remotely generate and transmit a resistance profile to the subject's monitoring station 400 via the communications link 170 whereby the resistance profile encountered by the subject varies as a function of time. The physician may also advantageously monitor both the physiologic parameters and the appearance of the subject, the latter via the video and audio capability described herein with respect to FIG. 5.

While the embodiment of FIG. 4 utilizes a pair of movable footrests as the exercise device, it will be appreciated that the invention as set forth herein may be adapted to other types of exercise equipment. For example, the monitoring station may be adapted to an exercise "bicycle" upon which the subject sits, to a treadmill upon which the subject walks, to a "stair-stepper" device, to a seated rowing machine, or even to a machine geared toward exercise of one specific portion of the body (such as the subject's arms or legs).

Respiration parameters may also be monitored on this or any other embodiment using any number of well known techniques such as spirometry or simple end-tidal $CO_2$ monitoring.

Furthermore, the invention disclosed herein may be adapted to other types of environments, such as within a moving vehicle such as an automobile, ambulance, or aircraft. The monitoring station 100 may also be made permanent, such as being built into the architecture of the subject's home or office, or otherwise integrated with other existing structures.

Figure 5:
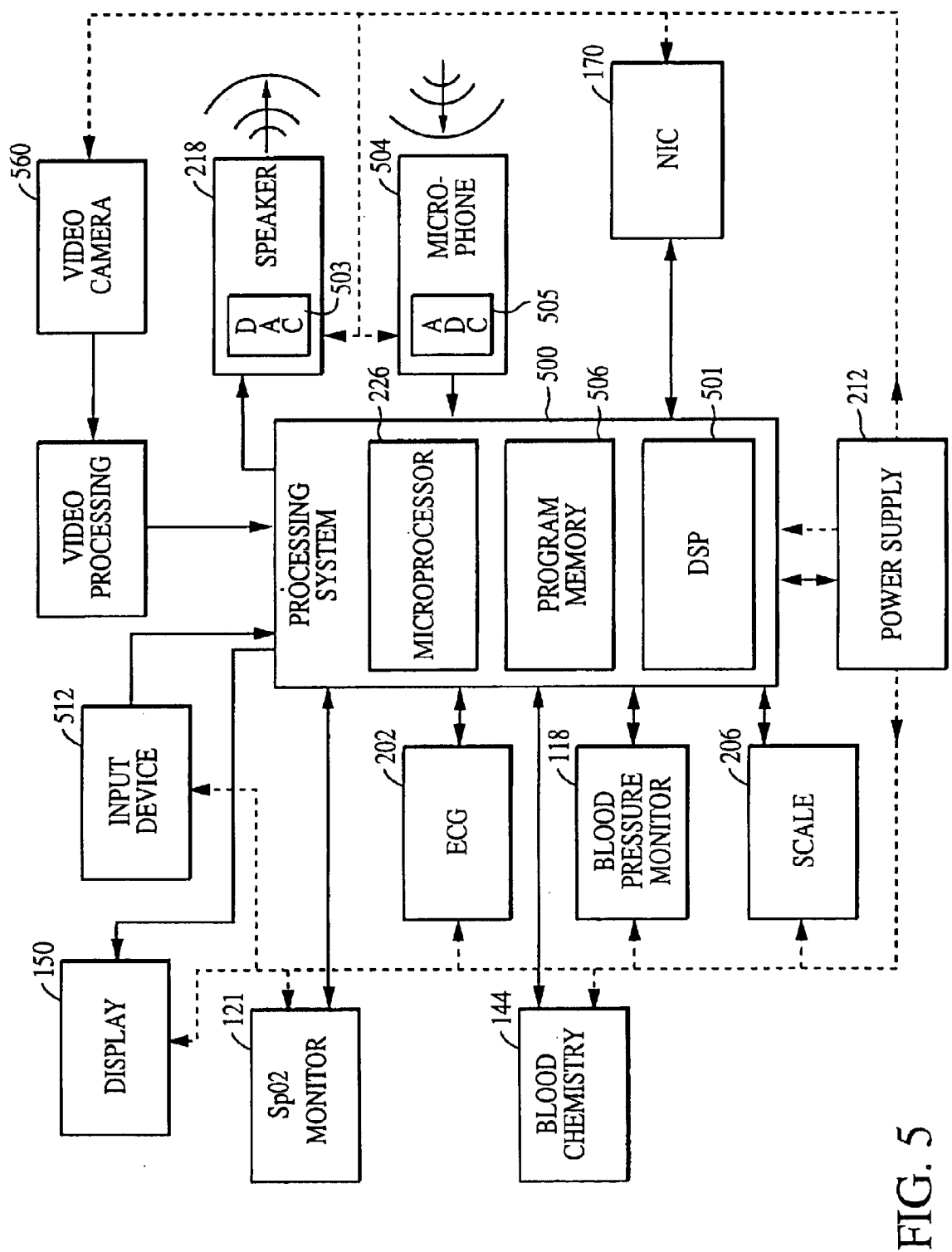
FIG. 5 is a functional block diagram of an alternative embodiment of the apparatus for monitoring physiologic parameters of a living subject according to the invention, the apparatus including a digital signal processor, speech recognition and text-to-speech (TTS) algorithms, and videoconferencing protocol stack.

FIG. 5 illustrates a second embodiment of the monitoring station 100. In the embodiment of FIG. 5, the processing system 500 is equipped with a digital signal processor (DSP) 501, and microphone 504 and associated ADC 505, in addition to the components shown in FIG. 2. Text-to-speech (TTS) and speech recognition algorithms (not shown) in the form of object code stored in program memory 506 and running on the DSP 501 are also provided. A Hidden Markov Modeling (HMM) speech recognition algorithm of the type well known in the art is used in the present embodiment, although other types may be substituted. The structure and operation of such speech recognition and TTS algorithms are well known, and accordingly will not be described further herein. In one mode of operation, verbal communication from the subject is converted into an analog waveform by the microphone 504, and converted into a digital format by the ADC 505. The digitized audio signal is then reduced to a compressed digital audio file (e.g., Code Excited Linear Prediction (CELP), .WAV, Audio Interchange File Format (AIFF), MP.3, or comparable) which is ultimately sent to one or more recipients via the communications system (FIG. 9), decompressed, and converted to an analog audio representation of the subject's voice via an audio speaker at the remote location(s). Alternatively, in another mode of operation, the subject's voice input may be used as the input to the aforementioned speech recognition algorithm which converts the subject's speech to a textual representation comprising machine-readable characters. This digital representation is then transmitted to the recipient, wherein the recipient may "read" the textual representation (much like an ordinary text-based e-mail), or alternatively synthesize audible speech using a text-to-speech (TTS) module and speaker within the recipient's terminal. In a third mode of operation, the subject may type in a textual message via a keyboard 512 provided with the system 500; this text message is transmitted and subsequently converted to a digital audio file which is then played over the audio system of the remote station(s). Such an approach is especially useful where the subject is unable to speak, or otherwise suffers from a speech impediment which makes communication difficult.

Similarly, voice or text messages originating from one or more remote locations may be converted to a compressed voice or textual format as just described, for playback over the audio speaker 502 (and associated DAC 503) or on the display device 150 (in the case of a speech-to-text message) of the subject's monitoring station. TTS capability such as that described herein would allow even blind subjects to operate the monitoring station via verbal instructions communicated to them remotely from the caregiver, or via stored CELP files resident in the monitoring station or remote database.

In fact, it will be recognized the monitoring station of the present invention may be so configured that the entire monitoring process is automated, whereby a subject need merely sit in the support member (or stand on the platform) of the monitoring device, their weight closing a switch which enables either the automatic collection of data, or the playback of a series of audible/visible instructions for the subject to follow. Many such alternatives are possible, each being within the scope of the invention described herein.

In addition to the foregoing TTS and speech recognition capabilities, the processing system 500 of FIG. 5 further includes audio/videoconferencing capability so as to facilitate observation of the subject during monitoring by the caregiver. In the present embodiment, this capability comprises an H.323 protocol "stack" of the type well known in the data networking arts, such as that produced by elemedia, a division of Lucent Technologies, Inc., which is used in conjunction with a video camera 560 mounted on the monitoring station 100. The components of the system 500 are configured to provide sufficient communications bandwidth to permit such conferencing to occur in real time or near-real time. When used with a compatible data network (e.g., that of FIG. 10 described below) and complementary audio/videoconferencing stack present at the remote location(s), the subject and one or more caregivers at different locations may advantageously remain in voice and video communication during the monitoring period. The system 500 may further be equipped with "digital whiteboard" capability of the type well known in the art, to facilitate the communication of graphical data, such as the caregiver circling or otherwise annotating information of interest to the subject interactively.

Computer Program and Display

Figure 6B:
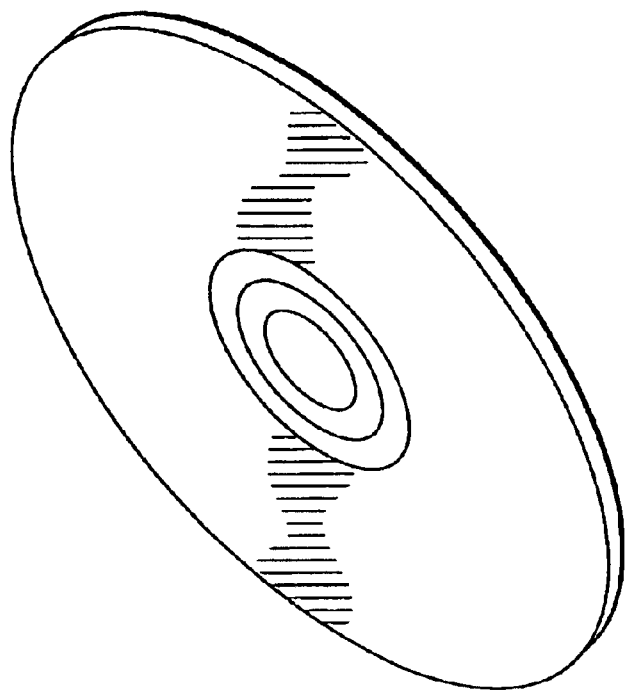
FIGS. 6a–6b are perspective views of various machine readable media having object code representations of computer programs incorporating the methods of the present invention.
Figure 6A:
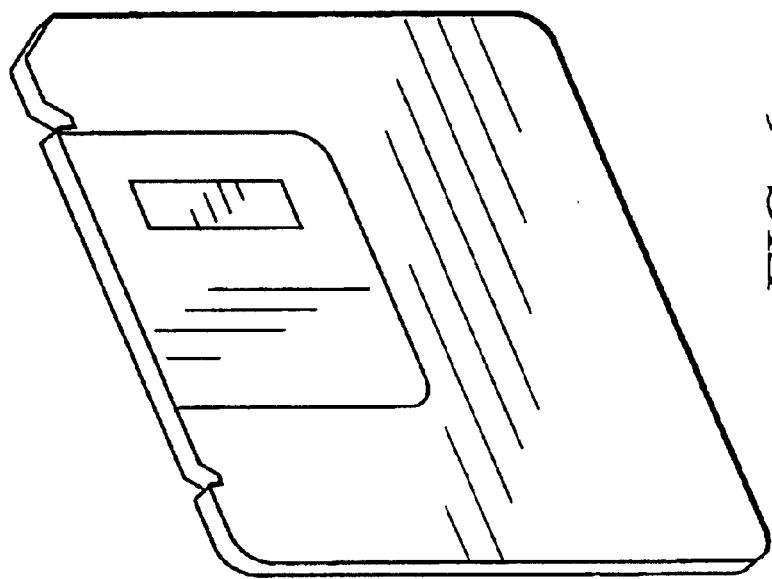

A computer program for implementing the analysis, display, and communications functionality is now described. In one exemplary embodiment, the computer program is an application program and comprises an object ("machine") code representation of a $C^{++}$ source code listing. While $C^{++}$ language is used for the present embodiment, it will be appreciated that other programming languages may be used, including for example VisualBasic™, Fortran, and $C^+$. The object code representation of the source code listing is compiled and disposed on a media storage device of the type well known in the computer arts, as illustrated in FIGS. 6a–b. Such media storage devices can include, without limitation, optical discs, CD ROMs, magnetic floppy disks or "hard" drives, tape drives, or even magnetic bubble memory. The storage device is utilized in conjunction with the monitoring station 100 (e.g., the PC or portable data processing device of the subject), the remote communications terminal (FIGS. 9–11), or both. The computer program further comprises a graphical user interface (GUI) which facilitates display and analysis of the monitored data, which is described below with respect to FIG. 8.

Figure 10:
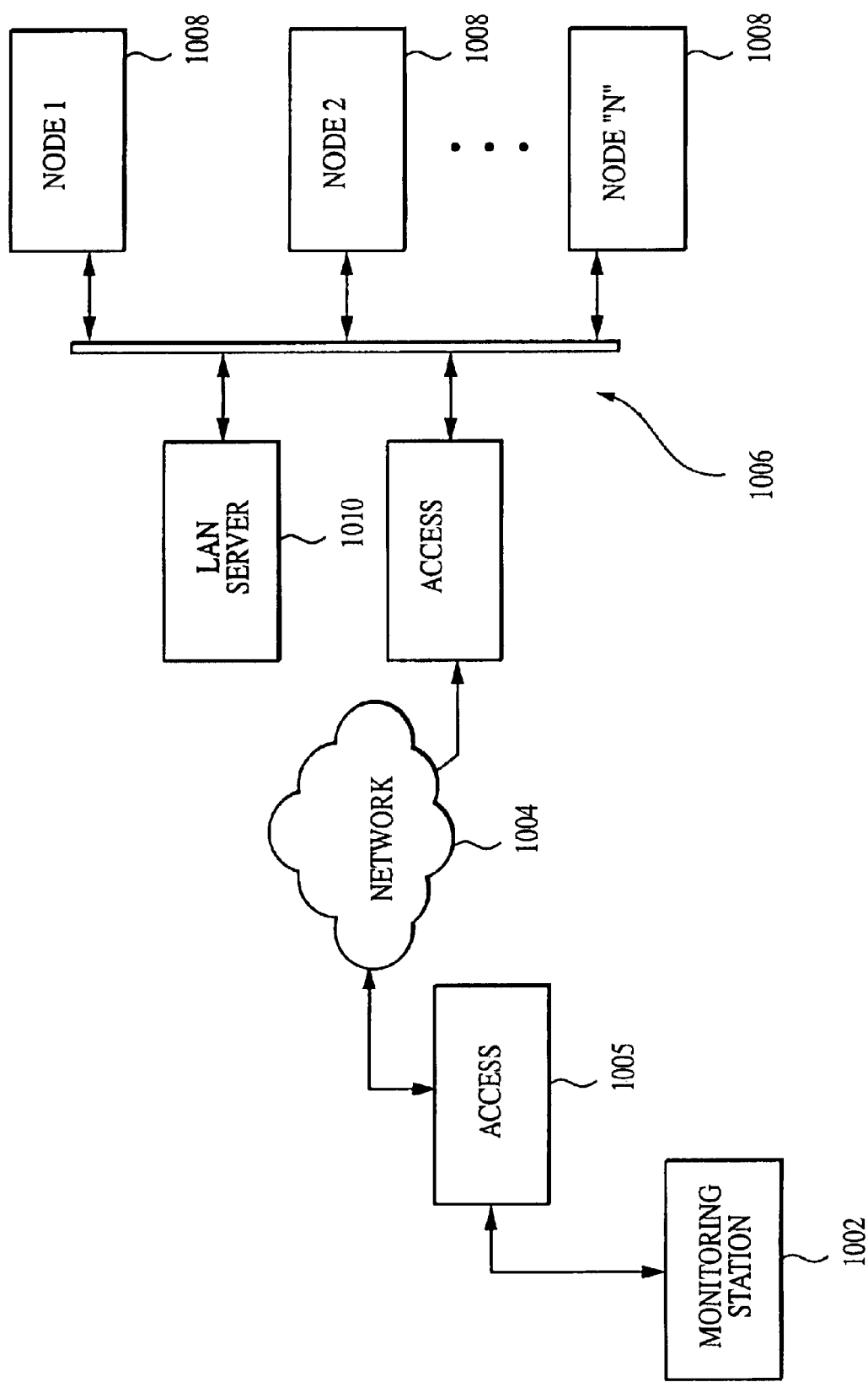
FIG. 10 is a functional block diagram of a second embodiment of the system for communicating medical information, the system employing a packet switched digital network having a plurality of nodes whereby remote processing and accessing of information may be accomplished.

In terms of general structure, the program is in one embodiment comprised of a series of subroutines or algorithms for analyzing, displaying, and transferring data derived from measured parametric data provided to the host system via a variety of inputs, including (i) the various monitors associated with the monitoring station 100; (ii) data input by either the subject or remote caregiver(s); and (iii) data obtained from other sources, including remote databases. FIG. 10 below shows one exemplary architecture employing each of these data sources.

In a second embodiment, the computer program comprises an assembly language/micro-coded instruction set disposed within the embedded storage device, i.e. program memory, of a digital signal processor (DSP) or microprocessor associated with the foregoing processing system 500 of FIG. 5. In this embodiment, the functionality of the computer program is fully integrated within the monitoring station and associated processing system 500, thereby making it effectively a "stand-alone" device. The computer program is stored in the form of a machine-readable object code representation in the RAM 230 and/or mass storage device 239 for use by the processor 226 during parametric assessment. The subject (and/or caregiver, if remote operation is utilized) configures the monitoring station by selecting one or more functional modes for the computer program and associated parametric monitors via the program GUI displays (FIG. 8) and the input device(s) 241. As measurements are obtained during the monitoring interval, the results of the analyses performed by the algorithms within the program or otherwise associated with the monitoring station 100 are displayed for viewing by the subject and caregiver. Such data generated by the program are also optionally stored in the storage device 239 for later retrieval, or output to an external device such as a printer, remote data storage unit, other peripheral component via a serial or parallel port (not shown) if desired.

It will be recognized that the computer program of the present invention may be adapted for use in any number of different software and hardware environments depending on the needs of the user, and the configuration of the monitoring station 100 and remote communications terminal. For example, the present invention may be adapted to run on Microsoft Windows™ (e.g., Windows 95, 98, NT, 2000) based machines, Apple Macintosh™ (system 8.0 and above), Linux, and most varieties of Unix (including but not limited to Sun Solaris™, IBM AIX, HP/UX, DEC ULTRIX™ and others). Additionally, a Java™-based version of the program may be used to embed information in web pages. Each user may download the version adapted for his/her equipment and operating system.

Figure 7:
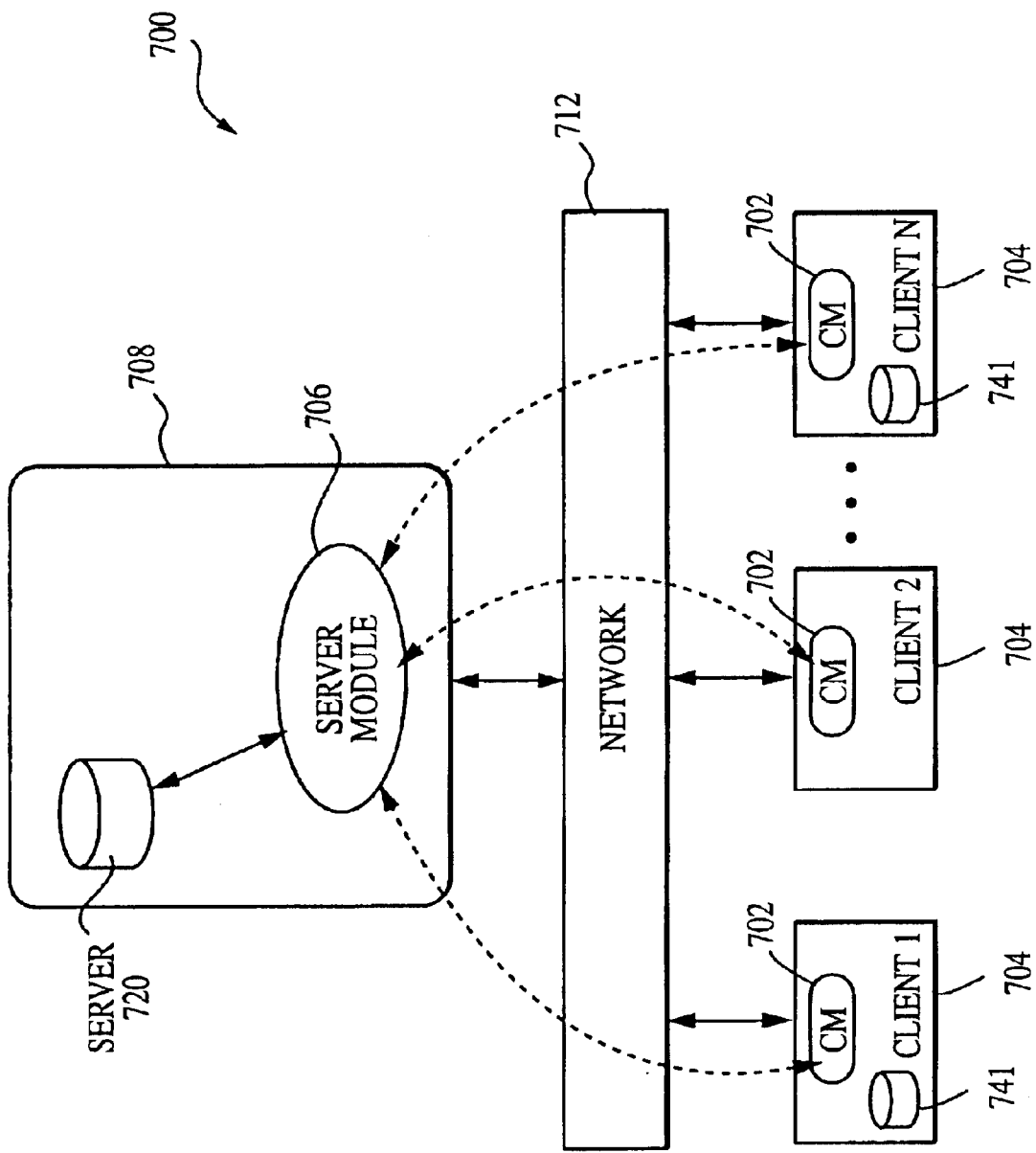
FIG. 7 is a functional block diagram of one embodiment of an object-oriented distributed application architecture according to the invention.

In a third embodiment shown in FIG. 7, the computer program and associated architecture 700 of the present invention comprises an object-oriented distributed application which comprises a plurality of client components or modules 702 distributed at a variety of subject locations 704, and at least one server component 706 disposed on one or more servers 708 located at a central medical facility, whereby the client components 702 interact and communicate with the server component(s) 706 via one or more interposed data or cable networks 712. A database 720 resident at the server 708 (or at another, remote location if desired) provides data to and stores data generated by the distributed application. Local databases 741 resident at each client device may also be used if desired to store, inter alia, data and information relating to a specific subject or transactions relating thereto.

The distributed application architecture of FIG. 7 has the advantage of utilizing less sophisticated, resource-intensive, and costly client (patient) devices, and simpler software to support those devices, since a substantial portion of the functionality of the distributed application is resident on the server(s) 708. Furthermore, distributed applications greatly facilitate state management of the client devices (monitoring stations 100). The structure and operation of object-oriented programming and distributed applications (such as the well known common object request broker architecture, or CORBA) are well known in the networking arts, and therefore are not discussed further herein.

Figure 8:
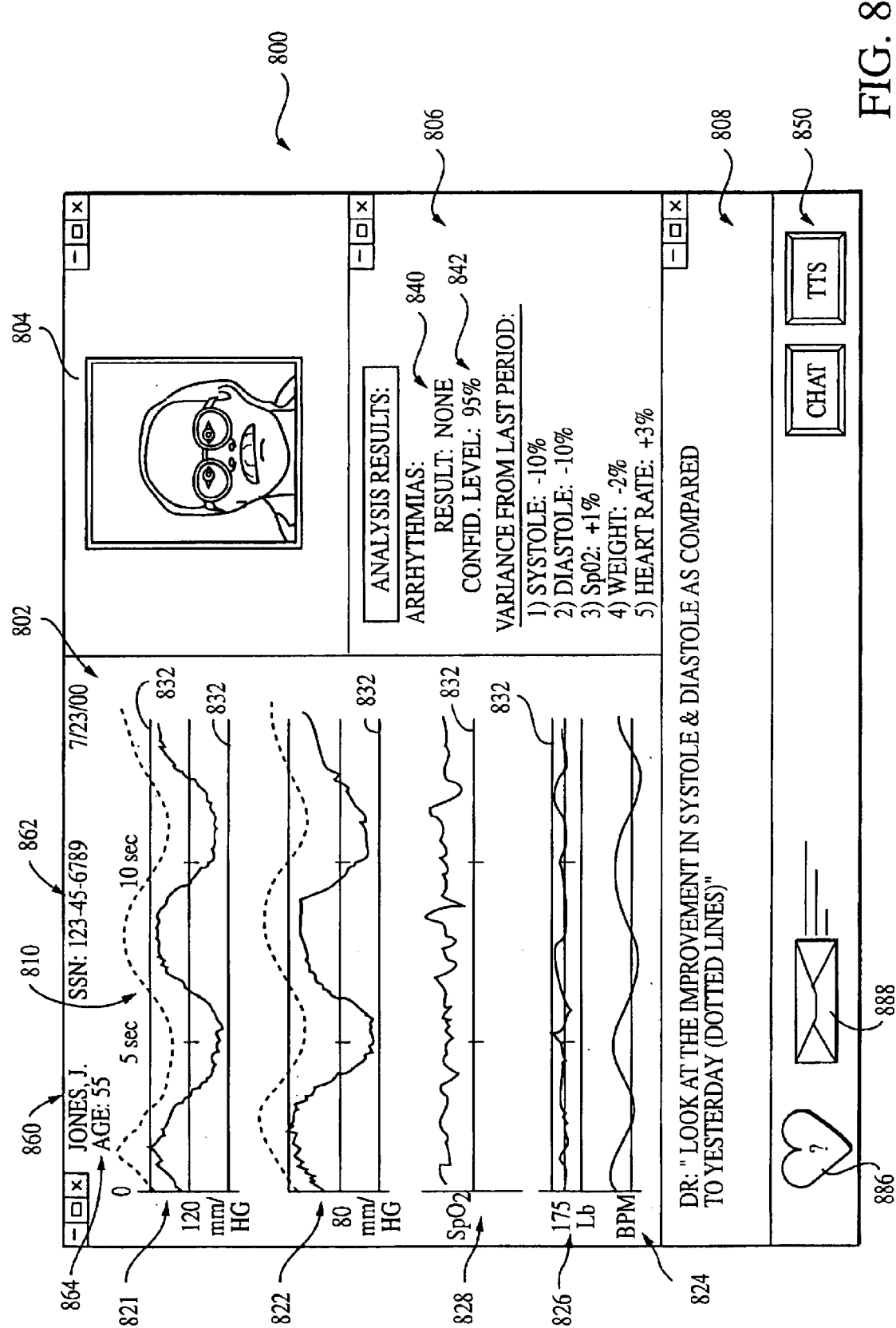
FIG. 8 is a graphical representation of an exemplary embodiment of the display format of the present invention used to provide medical data and other information to the subject(s) and caregiver(s).

Referring now to FIG. 8, the improved information display according to the invention is described. As illustrated in the exemplary embodiment of FIG. 8, the display 800 comprises a first viewing area or window 802, a second viewing window 804, a third viewing window 806, and a text message box 808. It will be recognized that while FIG. 8 illustrates windows of certain sizes and positions, such sizes and positions may be varied if desired. Furthermore, it will be recognized that one or all of the windows may be "minimized" or "maximized", and "activated" such as by placing a cursor on the desired window and clicking a mouse or other input device, as in the well known Windows ® operating system manufactured by Microsoft Corporation. The windows 802, 804, 806, 808 may as another alternative be displayed in a multiplexed or time-sharing fashion. Many other such alternatives are possible.

In the illustrated embodiment, the first window 802 comprises a plurality of parametric scales 810 which are used generally to display the signal or waveform associated with a monitored physiologic parameter as a function of another variable (e.g., time). Five different parameters (i.e., systolic/diastolic blood pressure (mm Hg) 821, 822, heart rate (BPM) 824, weight (lbs.) 826, and SpO2 828, are illustrated, being displayed as a function of time. The duration or monitoring interval 830 illustrated is 15 sec., although this may be varied to any value as previously discussed. The scales 810 optionally further include indicators 832 of the allowable values of a given parameter. For example, the systolic blood pressure value may have an allowable band for a given subject of between 100 and 140 mm Hg; values of systolic blood pressure measured by the blood pressure monitor which fall outside this band will be detected by the analysis algorithms previously described, and an alert sent to the remote communications terminal and displayed on the display device 150 of the subject's monitoring station 100.

The second window 804 of the display 800 comprises a videoconferencing display which shows the user of the display (i.e., subject, caregiver, etc.) an image obtained through the aforementioned videoconferencing software stack and video camera 560. Depending on the available bandwidth of the network connection, other information (such as audio and digital whiteboard) may be streamed between the various locations as well.

The third window 806 comprises an analysis window where the results of various analyses performed by the algorithms resident in the monitoring station 100 (or remotely) may be viewed. For example, using the aforementioned arrhythmia algorithm, ECG data obtained from the subject via the handgrips 112 and footrests 114 of the monitoring station 100 are analyzed using the processing capability resident within the processing system 210. The results of this analysis, such as in the form of a finding (e.g., "Arrhythmia detected" or "Arrhythmia not detected") 840 and an associated confidence value for the finding 842, are displayed to both the subject on the display device 150 of the monitoring station, and also transmitted via the communications device 170 to one or more remote communications terminals for display thereon contemporaneously. Alternatively, the third window 806 may be used to display the instantaneous value of the physiologic parameters being measured, data from past monitoring periods, "normal" or average values, etc.

The text message box 808 of the display is used, inter alia, to alert the user to the presence of incoming data or text messages, and for the display of relevant text. For example, the caregiver may wish to send the subject a personal note, status update, or other information via the communications link without requiring the subject to open separate e-mail management software while being monitored. Using the present invention, the party generating the message may type in (or speak) the desired message, which is then transmitted in a predetermined message protocol, and received by the message recipient, processed, and displayed on their display unit as text in the text message box 808. Hence, the text message function of the present invention functions interactively and in analogous fashion to the well known prior art "chat" commonly conducted over the Internet.

The display 800 also includes a plurality of icons 852 contained within a fourth area 850 and used for performing certain predetermined functions within the computer program. The icon structure is simplified and dedicated function icons are used to the maximum extent practicable for ease of operation, especially by the subject. For example, a first icon 856 resident on the display 800 is used to initiate the monitoring of a subject based on a predetermined set of physiologic parameters, monitoring interval, remote caregiver, etc. The user simply touches the area on the display device 150 corresponding to the desired function, and the capacitive screen translates this change in capacitance into the initiation of one or more algorithms within the program and operating system of the processing system 210, 500. In the illustrated example of FIG. 8, the "heart" icon 886 corresponds to monitoring of the subject's ECG and blood pressure, and the "envelope" icon 888 to transmission of the data to a remote location, although it will be recognized that myriad other symbols and arrangements may be used. Similarly, labeled keys 856 may be used to perform specific functions, such as the "Store Data" key in the illustrated embodiment, which is used for storing the results of a given monitoring session to a storage device. The generation and operation of iconbased functionality in computer programs and displays is well understood in the programming arts, and accordingly is not further described.

Program functionality may also be accomplished remotely as well, such as by the caregiver initiating monitoring of a subject at a different location via their local touch-screen display and the aforementioned communications link.

In addition to the foregoing, it will be recognized that the display 800 of the invention may be augmented with other data and information, such as for example the subject's name 860, SSN 862, age 864, treatment history, or other pertinent information System for Exchanging Data FIG. 9 illustrates a first embodiment of the system for exchanging medical information according to the present invention. The system 900 generally comprises a circuit switched network having a monitoring station 902 of the type described with respect to FIGS. 1–5 herein, a first public switched telephone network (PSTN) local access loop 904 which provides access from the subject's location to the PSTN; a PSTN transmission system 906 comprising a landline, microwave, or optical network, a communications terminal 908 disposed at a location different from that of the monitoring station 902, and a second local access loop 910 which provides access to the PSTN for the terminal 908. Also included are modulator/demodulator (modem) apparatus 912, 914 disposed at the general location of the monitoring station 902 and the communications terminal 908, respectively, to facilitate the transmission of the digital data signals generated by the monitoring station 902 and the communications terminal 908 across the analog portion of the PSTN/local loops. The communications terminal 908 of the illustrated embodiment comprises a personal computer (PC) of the type well known in the art, which is equipped with a modem device 914 and software necessary to transmit and receive data over the PSTN.

Alternatively, the local loops 904, 910 of the embodiment of FIG. 9 may be replaced by digital subscriber line (DSL) connections and modems of the type well known in the data networking arts; such DSL connections provide enhanced bandwidth and therefore data transmission speeds as compared to their analog predecessors.

In one embodiment of the system, the subject's personal computer (PC) is used as the interface with the PSTN via a standard 56 Kbps modem. A wireless RF or IR transceiver (such as the aforementioned "Bluetooth" device) is installed as a peripheral device on the subject's PC; data is streamed between the monitoring station 902 and the PC via the transceiver, and communicated to/from the PSTN via the modem on the PC. Selected portions of the data are also advantageously copied onto a designated storage device on the PC (such as its hard drive) during use; in this fashion, the subject may retain copies of their data for various monitoring periods, as well as data provided by the remote communications terminal, for subsequent viewing and analysis. Algorithms capable of identifying, storing, and subsequently analyzing the stored data as set forth above are well known to those of ordinary skill in the computer programming arts, and accordingly are not described further herein. Note that using this configuration, the subject and caregiver may also exchange information via standard e-mail if desired (i.e., via the subject's and caregiver's mail servers and an interposed data network).

It will further be recognized that the aforementioned functionality may be integrated entirely within the monitoring station 902. For example, the monitoring station may be provided with a keyboard and/or other input device, modem, etc. which allow the subject to perform all functions necessary to obtain data via the station 602 and exchange this data and other information (such as voice data or textual messages) with the remote communications terminal while sitting/standing at the station.

In yet another embodiment, the RF/IR transceiver previously described is coupled and in data communication with a portable data processing device. As used herein, the term "portable data processing device" will be understood to include any device capable of processing digital data, including, inter alia, laptop personal computers (PCs), PDAs such as the well known "Palm™" series manufactured by 3COM Corporation, so-called "hand-held" PCs such as the HPW-600ET "ePlate" incorporating Microsoft Windows CE manufactured by Hitachi Corporation, cellular telephones, and "smart" pagers. Subject data is loaded into the storage area of the potable device via an interface or I/O port on the device; this data is later retrieved from the device for analysis by the subject or a caregiver at a remote location. Alternatively, the caregiver may load information/data into the portable device at the remote location (such as when the subject arrives for a routine visit), such information then being communicated from the storage area of the portable device to the monitoring station 902 for use thereby. In one example, the caregiver could provide the subject a pre-programmed exercise profile as previously discussed with respect to the apparatus of FIG. 4. Alternatively, the caregiver could provide the subject with electronic guidelines or instructions for operation of the monitoring station which would be displayed on the display device 150 of the station 100, or via the audio system 502, 503 of the station. As yet another alternative, the caregiver may provide the subject with an audio/visual analysis of their condition conducted by a physician. As yet a further alternative, the caregiver may provide the subject with a revised set of physiologic limit values which would be displayed for the subject, and automatically programmed into the system during subsequent operation by the subject. Many other alternatives are possible.

Figure 11:
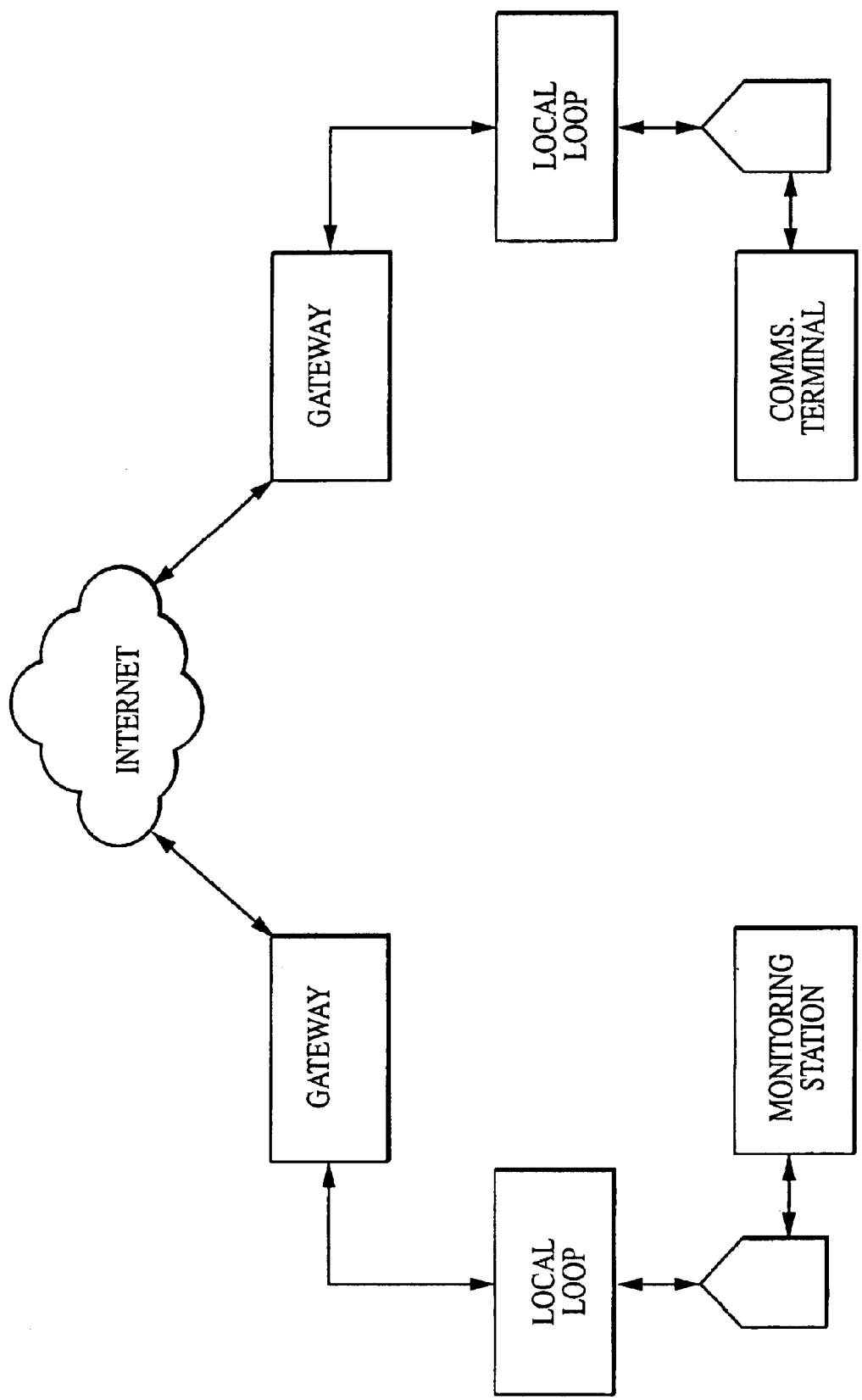
FIG. 11 is logical block diagram illustrating the structure of a typical voice over IP (VOIP) network which may be used to transmit information including voice data between the subject and one or more remote locations.

FIG. 10 illustrates a second embodiment of the system for exchanging information according to the invention. In this embodiment, the monitoring station 1002 is coupled to a packet switched digital data network 1004 such as the Internet via an access provider 1005. A local area network 1006 is also coupled to the digital data network 1004, the former comprising a plurality of different remote nodes 1008 and at least one server 1010 each operatively connected to the network 1006, although it will be appreciated that other configurations having more or less nodes, architectures, and/or servers may be employed consistent with the invention. Hence, the term "computer network" as used herein may include, but is not limited to, local-area networks (LAN), wide-area networks (WAN), intranets, the Internet, and may utilize any topology, protocol, or physical medium for communication including Ethernet, X.25, token ring, frame relay, ATM, SONET. Hence, as used herein, the term "computer network" is meant in its broadest sense to include any type of network capable of transmitting digital data between users. For example, the well known voice over internet protocol (VoIP), which utilizes an IP network and a series of interposed gateways to transfer information from the local loop of the subject to that of the remote station(s) as illustrated in FIG. 11, may be used to transfer voice data and other information if desired.

Method of Monitoring Physiologic Parameters

Figure 12:
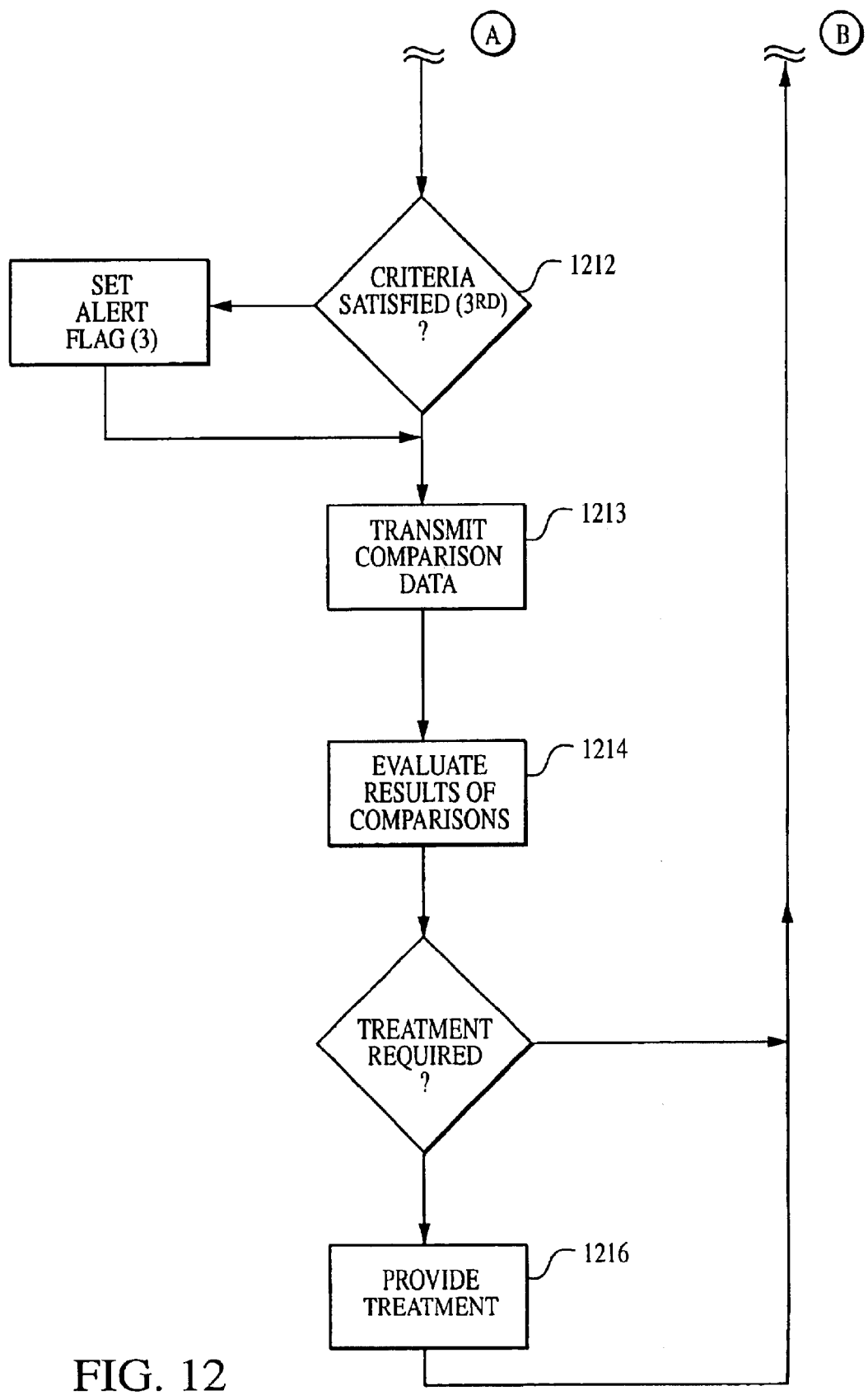
FIG. 12 is a logical flow diagram illustrating one exemplary embodiment of the method of monitoring the physiologic parameters of a living subject according to the invention.

Referring now to FIG. 12, the method of monitoring physiologic parameters according to the present invention is described. In the embodiment of FIG. 12, the method 1200 comprises measuring a first physiologic parameter from a blood vessel of the subject per step 1202; measuring a second physiologic parameter from the subject per step 1204; measuring a third physiologic parameter from the subject per step 1206; comparing data derived from the measurements of the first, second, and third physiologic parameters to predetermined values of those parameters, respectively (step 1208); and identifying when at least a portion of the data bears a predetermined relationship to at least one of the predetermined values (steps 1210, 1211, 1212). In the embodiment of FIG. 12, the first parameter measured comprises blood pressure, the second heart rate (as derived from ECG measurement), and the third the weight of the subject, although it will be recognized that different, fewer, or additional parameters may be measured. As previously described, the monitoring station is programmed with predetermined values or ranges of values acceptable for the given subject; these values may be either entered by the subject, entered remotely via a caregiver at a remote location using a communications terminal as in FIG. 9, or entered via a pre-programmed portable device such as discussed above. These values are compared to the measurements obtained from the subject via the foregoing apparatus, and the relationship between the measured data and acceptable values/ranges identified. The subject's caregiver is provided the results of this comparison via a communications channel per step 1213 so as to permit ongoing evaluation of the subject's condition from a remote location in real time per step 1214. The caregiver may then recommend and implement a course of treatment for the subject, and/or additional monitoring, via the aforementioned communications channel per step 1216.

It is noted that many variations of the methods described above may be utilized consistent with the present invention. Specifically, certain steps are optional and may be performed or deleted as desired. Similarly, other steps (such as additional data sampling, processing, filtration, calibration, or mathematical analysis for example) may be added to the foregoing embodiments. Additionally, the order of performance of certain steps may be permuted, or performed in parallel (or series) if desired. Hence, the foregoing embodiments are merely illustrative of the broader methods of the invention disclosed herein.

It is further noted that while the foregoing description has been cast in terms of CHF patients, other classes of subjects may benefit from the apparatus and methods disclosed herein. For example, chronic obstructive pulmonary disease (COPD) patients often are in need of oxygen or related therapies for maintaining their daily life "status quo". Cardiac arrhythmia or pacemaker/ICD patients can also benefit from the system and methods to provide their caregivers with updated information about their cardiovascular status. Likewise, patients retuning home from serious illnesses or injury requiring medication, rest or nursing care are also possible candidates to employ the system described herein.

While the above detailed description has shown, described, and pointed out novel features of the invention as applied to various embodiments, it will be understood that various omissions, substitutions, and changes in the form and details of the device or process illustrated may be made by those skilled in the art without departing from the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. A method of monitoring a plurality of physiologic parameters within a living subject, comprising:

continuously and tonometrically measuring blood pressure from a blood vessel of said subject without using a cuff, said act of measuring further comprising:
(i) measuring a first hemodynamic parameter from a blood vessel of said subject;
(ii) compressing said blood vessel;
(iii) measuring a second hemodynamic parameter from said blood vessel during at least a portion of said act of compressing;
(iv) identifying at least one artifact within said second hemodynamic parameter; and
(v) calibrating the first hemodynamic parameter using at least said artifact;

measuring a second physiologic parameter from said subject;

measuring a third physiologic parameter from said subject;

comparing data derived from said acts of measuring to predetermined values of said blood pressure, second, and third parameters, respectively; and identifying when at least a portion of said data bears a predetermined relationship to at least one of said predetermined values.

2. The method of claim 1, wherein the acts of measuring said three physiological parameters are performed simultaneously.

3. The method of claim 1, wherein the acts of measuring said second and third physiologic parameters comprise measuring the weight of said subject and measuring the electrocardiograph of said subject via at least two electrically conductive terminals adapted to contact the extremities of said subject, respectively.

4. The method of claim 3, further comprising measuring the oxygen saturation of the blood of said subject.

5. The method of claim 3, wherein the act of identifying comprises alerting the subject using a technique selected from the group consisting of a visual alert and an audible alert.

6. The method of claim 3, wherein the act of identifying comprises:

generating a data set representative of the relationship of said data associated with at least one of said first, second or third parameters to corresponding ones of said predetermined values;

transmitting said data set via a communications channel to a receiver; and generating an alert at said receiver.

7. A device for monitoring the physiology of a living subject, comprising:

first apparatus adapted to continuously and tonometrically determine the arterial blood pressure from said blood vessel and generate first data relating thereto, said act of determining comprising forming a time-frequency distribution of acoustic energy transmitted into said artery;

second apparatus adapted to measure at least one other physiologic parameter from said subject and generate second data relating thereto, said physiological parameter selected from the group consisting of: (a) weight; (b) ECG; and (c) SPO2; and a digital processor operatively coupled to said first and second measuring apparatus and having a program running thereon, said processor and program adapted to process at least portions of said first and second data.

8. A method of monitoring a plurality of physiologic parameters within a living subject, comprising:

continuously and tonometrically measuring blood pressure from a blood vessel of said subject using controlled applanation of said vessel and without using a cuff, said act of measuring blood pressure comprising forming a time-frequency distribution of acoustic energy radiated into said blood vessel;

measuring a second physiologic parameter from said subject;

measuring a third physiologic parameter from said subject;

comparing data derived from said acts of measuring to predetermined values of said blood pressure, second, and third parameters respectively; and identifying when at least a portion of said data bears a predetermined relationship to at least one of said predetermined values.

9. The method of claim 8, wherein the act of measuring said three physiological parameters are performed simultaneously.

10. The method of claim 8, wherein the act of measuring blood pressure comprises:

tonometrically measuring a first hemodynamic parameter from a blood vessel of said subject;

measuring a second hemodynamic parameter from said blood vessel;

deriving a calibration function based at least in part on said second hemodynamic parameter; and calibrating the first hemodynamic parameter using said calibration function.

11. The method of claim 8, wherein the acts of measuring said second and third physiologic parameters comprise measuring the weight of said subject and measuring the electrocardiograph of said subject via at least two electrically conductive terminals adapted to contact the extremities of said subject, respectively.

12. A method of remotely assessing the physical condition of a living subject disposed at a first location, comprising:

continuously and tonometrically measuring the blood pressure from a blood vessel of said subject to produce first data, said act of measuring blood pressure comprising controllably applanating at least a portion of said blood vessel without using a cuff and forming a time-frequency distribution of acoustic energy radiated into said blood vessel;

measuring a second physiological parameter from said subject to produce second data;

measuring a third physiological parameter from said subject to produce third data;

transmitting at least a portion of said first, second, and third data to a second location; and assessing the physical condition of said living subject based at least in part on said data.

13. The method of claim 12, wherein the acts of measuring said physiological parameters are performed simultaneously.

14. The method of claim 12, further comprising:

generating at least one treatment option for said subject based on said act of assessing; and transmitting information relating to said at least one treatment option from a third location to said first location.

15. A system for monitoring the physiology of a living subject, comprising:

a first measuring apparatus adapted to continuously and tonometrically determine the blood pressure within an artery from said subject and form a time-frequency distribution therefrom, said first apparatus comprising at least one pressure transducer which also acts to controllably compress said artery without use of a cuff;

a second measuring apparatus adapted to measure at least one other physiologic parameter not directly related to said blood pressure from said subject and generate second data relating thereto, said second apparatus capable of measuring said second physiologic parameter contemporaneously with measuring said blood pressure;

a data processor operatively coupled to said first and second measuring apparatus and having a program running thereon, said processor and program adapted to process at least portions of said first and second data and compare said at least portions to other first and second data previously obtained from said subject, respectively; and display apparatus, in data communication with said at least one measuring apparatus, adapted to display at least a portion of said first and second data.

* * * * *